(12) United States Patent
Bochenko

(10) Patent No.: US 10,072,959 B2
(45) Date of Patent: Sep. 11, 2018

(54) FLOW SENSOR SYSTEM WITH CONNECTION ASSEMBLY

(71) Applicant: CRISI Medical Systems, Inc., Franklin Lakes, NJ (US)

(72) Inventor: Walter John Bochenko, Encinitas, CA (US)

(73) Assignee: CRISI Medical Systems, Inc., Franklin Lakes, NJ (US)

( * ) Notice: Subject to any disclaimer, the term of this patent is extended or adjusted under 35 U.S.C. 154(b) by 97 days.

(21) Appl. No.: 15/247,150

(22) Filed: Aug. 25, 2016

(65) Prior Publication Data

US 2017/0059376 A1    Mar. 2, 2017

Related U.S. Application Data

(60) Provisional application No. 62/211,287, filed on Aug. 28, 2015.

(51) Int. Cl.
*G01F 1/56* (2006.01)
*G01F 15/18* (2006.01)
(Continued)

(52) U.S. Cl.
CPC .............. *G01F 1/56* (2013.01); *A61M 5/00* (2013.01); *A61M 5/16804* (2013.01); *A61M 5/172* (2013.01); *G01F 1/667* (2013.01); *G01F 15/18* (2013.01); *G05D 7/0623* (2013.01); *A61M 2205/33* (2013.01); *A61M 2205/3334* (2013.01); *A61M 2205/3569* (2013.01)

(58) Field of Classification Search
CPC ....................................................... G01F 1/56
See application file for complete search history.

(56) References Cited

U.S. PATENT DOCUMENTS 4,299,336 A      11/1981  Studer
4,677,858 A  *   7/1987   Ohnhaus ................. G01P 5/165
                                                    73/861.65
(Continued)

FOREIGN PATENT DOCUMENTS

DE       102008055167 A1    7/2010
EP          0897102 A1      2/1999
(Continued)

*Primary Examiner* — Jewel V Dowtin
(74) *Attorney, Agent, or Firm* — The Webb Law Firm

(57) ABSTRACT

A system for sensing medicament delivery and transmitting an operation modification signal having at least two separable components is disclosed. The system includes a flow sensor having an inlet to couple to a fluid source, an outlet for delivering fluid from the fluid source to a patient, at least one sensor to characterize at least one attribute of the fluid, and at least one pin in in electrical communication with the sensor. The system includes a second component having a base having a contact, a controller in electrical communication with the contact that generates an operation modification signal in response to an attribute matching a condition specified by a rule, a transmitter for transmitting the operation modification signal to a device, the operation modification signal, when received by the device, causing the device to modify at least one operating parameter, and a cross-component electrical circuit.

34 Claims, 24 Drawing Sheets

(51) Int. Cl.
*A61M 5/00* (2006.01)
*A61M 5/168* (2006.01)
*A61M 5/172* (2006.01)
*G01F 1/66* (2006.01)
*G05D 7/06* (2006.01)

(56) References Cited

U.S. PATENT DOCUMENTS

| | | | |
|---|---|---|---|
| 5,048,798 A * | 9/1991 | Araki | G02B 6/4485 |
| | | | 254/134.4 |
| 5,463,906 A | 11/1995 | Spani et al. | |
| 6,155,463 A | 12/2000 | Dentler | |
| 6,981,960 B2 | 1/2006 | Cho et al. | |
| 7,032,435 B2 * | 4/2006 | Hassenflug | G01F 1/28 |
| | | | 340/603 |
| 7,255,006 B2 | 8/2007 | Spanke et al. | |
| 7,264,885 B2 | 9/2007 | Rosen et al. | |
| 7,560,494 B2 | 7/2009 | Steinbrenner et al. | |
| 7,782,202 B2 | 8/2010 | Downie et al. | |
| 7,882,751 B2 * | 2/2011 | Hoecker | G01F 15/185 |
| | | | 73/861.22 |
| 7,976,508 B2 | 7/2011 | Hoag | |
| 8,544,344 B2 | 10/2013 | Murakami | |
| 8,714,030 B1 | 5/2014 | Liu et al. | |
| 8,863,589 B2 * | 10/2014 | Bitto | G01F 1/8477 |
| | | | 73/861.355 |
| 8,904,878 B2 | 12/2014 | Wiest et al. | |
| 9,541,431 B2 | 1/2017 | Nakano et al. | |
| 2007/0034016 A1 | 2/2007 | Maginnis et al. | |
| 2009/0157040 A1 | 6/2009 | Jacobson et al. | |
| 2009/0270844 A1 | 10/2009 | Seeley et al. | |
| 2010/0063765 A1 | 3/2010 | Carlisle et al. | |
| 2011/0046514 A1 * | 2/2011 | Greenwald | A61B 5/208 |
| | | | 600/573 |
| 2014/0033827 A1 | 2/2014 | Satou et al. | |
| 2015/0204705 A1 | 7/2015 | Forster et al. | |
| 2015/0211904 A1 | 7/2015 | Forster | |
| 2016/0375449 A1 * | 12/2016 | Cao | B05B 1/341 |
| | | | 239/461 |

FOREIGN PATENT DOCUMENTS

| | | |
|---|---|---|
| EP | 2857803 A1 | 4/2015 |
| WO | 0209795 A2 | 2/2002 |
| WO | 2011126895 A2 | 10/2011 |
| WO | 2014016315 A1 | 1/2014 |
| WO | 2014016316 A1 | 1/2014 |

* cited by examiner

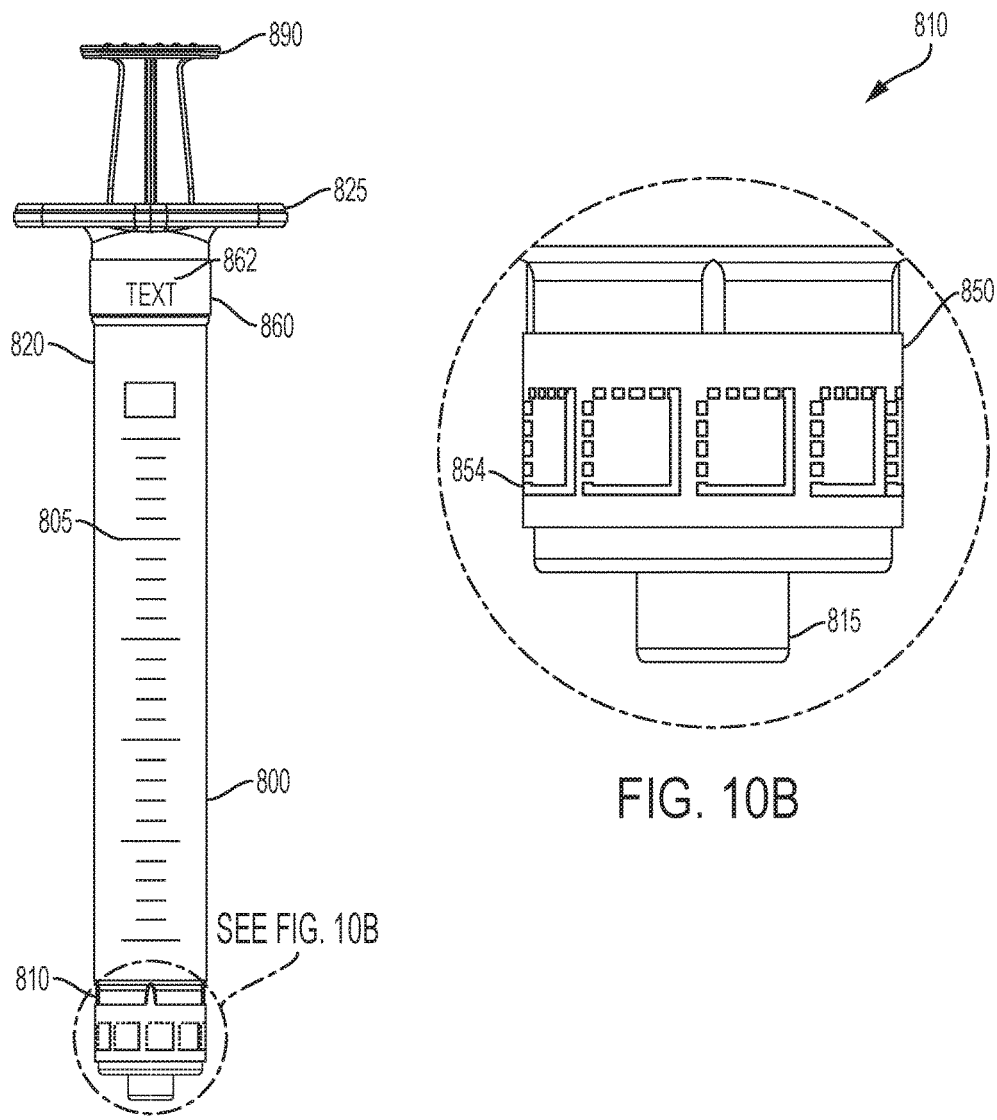
FIG. 10B
FIG. 10A
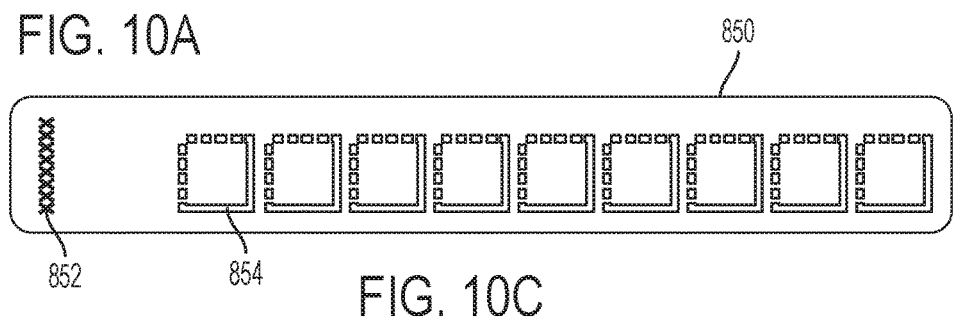
FIG. 10C

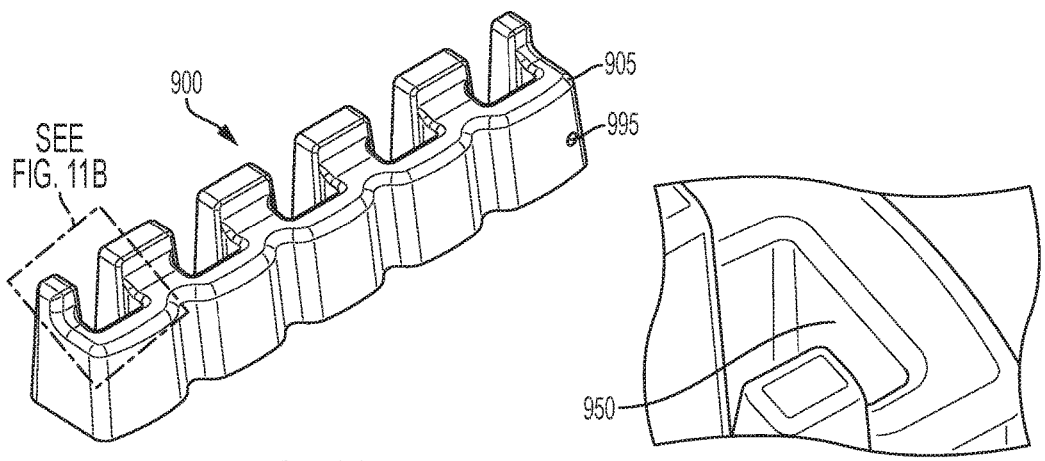
FIG. 11A
FIG. 11B
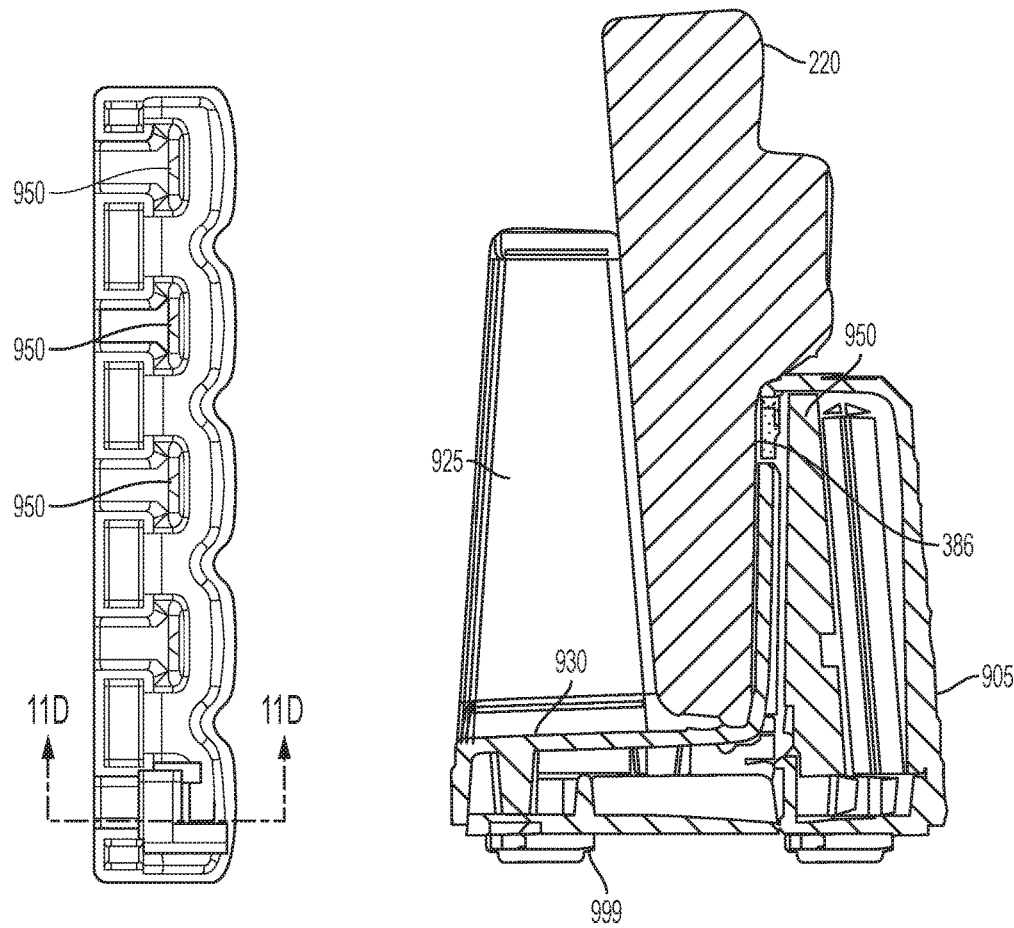
FIG. 11C
FIG. 11D

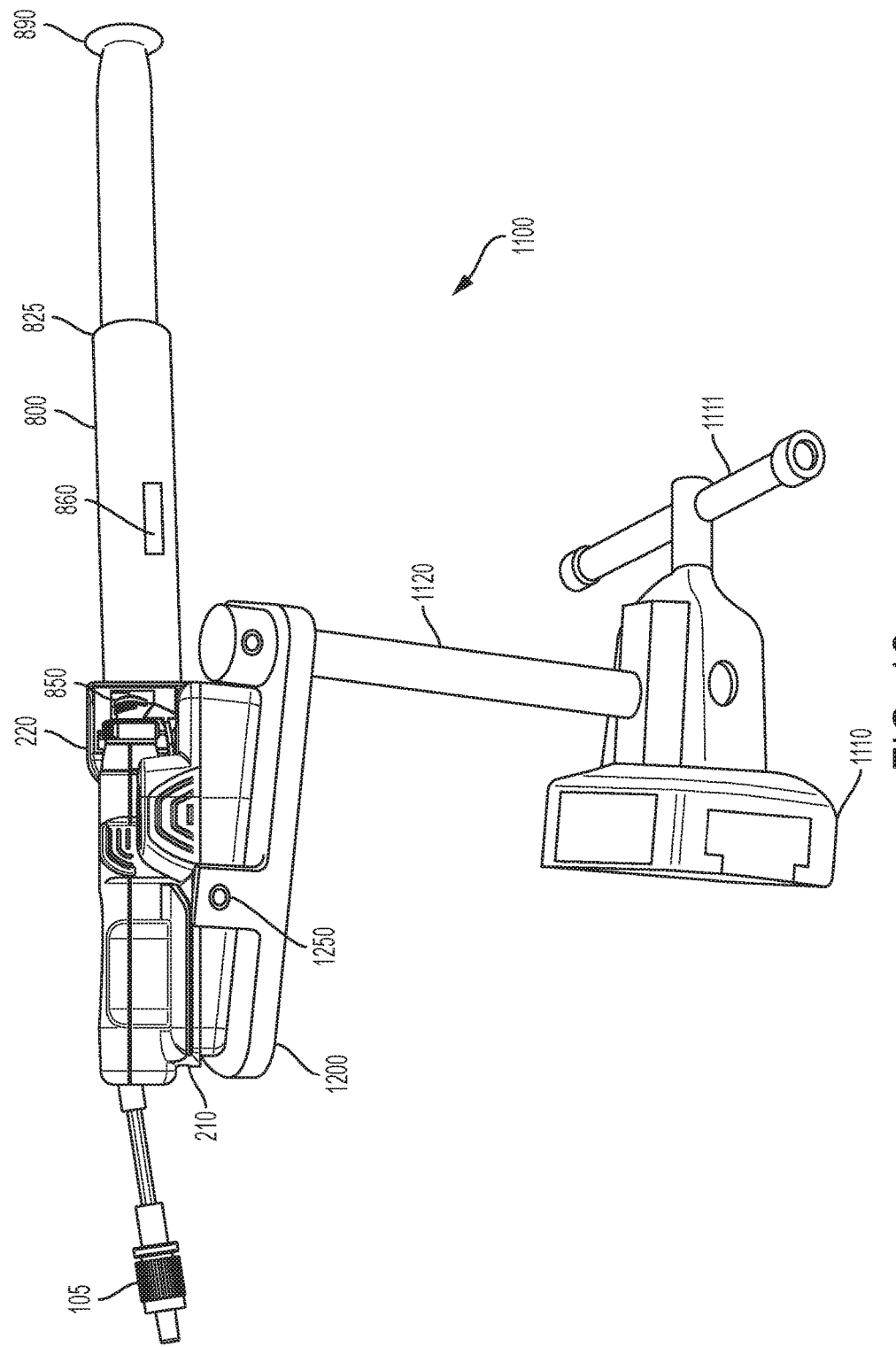

FLOW SENSOR SYSTEM WITH CONNECTION ASSEMBLY

CROSS REFERENCE TO RELATED APPLICATIONS

This application claims the benefit of U.S. Provisional Patent Application No. 62/211,287, filed Aug. 28, 2015, the disclosure of which is incorporated herein by reference in its entirety.

BACKGROUND OF THE INVENTION

Field of the Disclosure

The present disclosure relates generally to a flow sensor system. More particularly, the present disclosure relates to a flow sensor system for providing intravenous bolus injections of medication to a patient which provides healthcare professionals with an automated record of medication, concentration, volume, dose, and time of each injection. Preferably, the system has an ultrasonic flow sensor.

Description of the Related Art

There is a need to reduce medication error at bedside during bolus delivery. It would be advantageous to provide a record of, and electronically measure, bolus delivery which allows monitoring bolus delivery and automatic documentation of bolus delivery as part of a patient's health record. Additionally, it would be advantageous to provide alerts when bolus delivery inconsistent with a patient's medical record is about to occur.

SUMMARY OF THE INVENTION

The present disclosure provides a system for sensing flow of a fluidic medicament. The system includes an intelligent injection port which may attach to an injection site (such as a "Y Site" or a stop cock) for manually administered IV injections. The system includes two main sub-assemblies: a single-use flow sensor and a reusable base unit, which fit together prior to use.

In accordance with an embodiment of the present invention, a system for sensing medicament delivery and transmitting an operation modification signal having at least two separable components includes a first component and a second component. The first component includes a flow sensor having a fluid port having a flow tube, a fluid inlet at a first end of the flow tube adapted to couple to an outlet of a fluid source, and a fluid outlet at a second end of the flow tube adapted to deliver fluid from the fluid source to a fluid pathway that provides fluid to a patient. The first component also includes at least one sensor to characterize at least one attribute of the fluid from the fluid source, and at least one pin in electrical communication with the at least one sensor. The second component includes a base having at least one contact, and a controller in electrical communication with the at least one contact that generates the at least one operation modification signal in response to at least one attribute matching at least one condition specified by at least one rule. The second component also includes a transmitter for wirelessly transmitting the operation modification signal to at least one device, the operation modification signal, when received by the at least one device, causing the at least one device to modify at least one operating parameter, and a cross-component electrical circuit. The flow sensor is mountable onto the base and the cross-component electrical circuit is a connection made by the contacts engaging the pins.

In certain embodiments, the flow sensor also includes end fittings adapted for securing the flow tube to the end fittings and first and a second piezo elements that are mounted to the end fittings. The flow tube may be a stainless steel material. The first piezo element and the second piezo element may be annular in shape and encircle the flow tube at each respective mounting point.

The flow sensor may be disposed of after the flow sensor is used to generate one operation modification signal. The base may be used with a different flow sensor. In certain configurations, the flow sensor further includes cantilevered wings adapted for securing the flow sensor to the base. The flow sensor may include a follower and the base may include a cam wherein the follower follows at least a portion of the cam when the flow sensor is mounted to the base.

In other configurations, the flow sensor includes an opening and the base further includes a protrusion wherein the opening is sized and shaped to engage the protrusion and the protrusion enters the opening when the flow sensor is mounted to the base. The flow sensor may include an opening and the base may include a protrusion wherein the opening is sized and shaped to engage the protrusion and the cam is adapted to move the pin away from the protrusion while the protrusion enters the opening when the flow sensor is mounted to the base.

The flow sensor may include at least one cantilevered wing having a tab adapted for securing the flow sensor to the base by engagement of the tab to at least one lip in the base. The at least one cantilevered wing may be deflectable in a direction to allow the tab to release from the at least one lip, thereby allowing the flow sensor to become de-mounted from the base. The at least one cantilevered wing may be a pair of cantilevered wings. In certain configurations, the at least one cantilevered wing may be a pair of cantilevered wings and each respective wing may be arranged opposite each other and the opening is spaced away from the wings, and the opening has a center position which bisects a distance between the cantilevered wings and the at least one follower is a pair of followers and each respective follower is arranged opposite each other on the flow sensor. In another configuration, the at least one cantilevered wing is a pair of cantilevered wings and each respective wing is arranged opposite each other and the opening is spaced away from the wings, and the opening has a center position which bisects a distance between the cantilevered wings.

In certain configurations, the system further includes a seal for a liquid-tight engagement between the flow sensor and the base, wherein the seal surrounds the cross-component electrical circuit, thereby sealing the cross-component electrical circuit from contamination by a liquid. The flow sensor may also include cantilevered wings having a tab adapted for securing the flow sensor to the base by engagement of the tab to a lip in the base.

In accordance with another embodiment of the present invention, a system for sensing medicament delivery and transmitting an operation modification signal having at least two separable components includes a first component and a second component. The first component includes a flow sensor having a fluid port having a flow tube, a fluid inlet at a first end of the flow tube adapted to couple to an outlet of a fluid source, and a fluid outlet at a second end of the flow tube adapted to deliver fluid from the fluid source to a fluid pathway that provides fluid to a patient. The first component also includes at least one sensor to characterize at least one attribute of the fluid from the fluid source, and a movable detector which detects a coupling of the outlet of the fluid source to the fluid inlet of the flow sensor. The second component includes a base having a controller that generates the operation modification signal in response to at least one attribute matching at least one condition specified by at least one rule, a switch for activating said controller, and a transmitter for wirelessly transmitting the operation modification signal to at least one device. The operation modification signal, when received by the at least one device, causes the at least one device to modify at least one operating parameter. The flow sensor is mountable onto the base and the movable detector engages the at least one switch, thereby activating the controller.

In certain configurations the flow sensor further includes cantilevered wings adapted for securing the flow sensor to the base. The flow sensor may include a follower and the base further includes a cam wherein the follower follows at least a portion of the cam when the flow sensor is mounted to the base. The flow sensor may further include an opening and the base further includes a protrusion wherein the opening is sized and shaped to engage the protrusion and the protrusion enters the opening when the flow sensor is mounted to the base. The flow sensor may also further include an opening and the base further includes a protrusion wherein the opening is sized and shaped to engage the protrusion and the cam is adapted to move the pin away from the protrusion while the protrusion enters the opening when the flow sensor is mounted to the base.

The flow sensor may also include cantilevered wings having a tab adapted for securing the flow sensor to the base by engagement of the tab to a lip in the base. The detector may include a cantilevered beam protruding from a portion of the flow sensor. The cantilevered beam may have a free end which engages the switch by deflection of the cantilevered beam. Optionally, the detector may include a cantilevered beam protruding from a portion of the flow sensor, the cantilevered beam having a free end having an outlet engaging portion extending in a direction generally perpendicular to the cantilevered beam. The detector may also include a switch engaging portion of the free end extending in a direction generally opposite to the outlet engaging portion.

The flow sensor can include a vault that covers a portion of the base thus forming a protective layer to limit contamination of the reusable base from adhesive residue, blood spatter or other bodily fluids, dripping fluids from IV lines, and the like. In addition, the vault may allow for easier sterilization and cleaning for subsequent patient use.

In accordance with another embodiment of the present invention, a system for sensing medicament delivery and transmitting an operation modification signal having at least two separable components includes a first component and a second component. The first component includes a flow sensor having a fluid port having a flow tube, a fluid inlet at a first end of the flow tube adapted to couple to an outlet of a fluid source having a target, and a fluid outlet at a second end of the flow tube adapted to deliver fluid from the fluid source to a fluid pathway that provides fluid to a patient. The first component also includes at least one sensor to characterize at least one attribute of the fluid from the fluid source. The second component includes a base having a portal, a controller in communication with an optical sensor having an axis that extends through the portal and inputs a signal to the controller, and wherein the controller generates the at least one operation modification signal in response to at least one attribute matching at least one condition specified by at least one rule. The second component may also include a transmitter for wirelessly transmitting the operation modification signal to at least one device, the operation modification signal, when received by the at least one device, causes the at least one device to modify at least one operating parameter. When the flow sensor is mounted onto the base the optical sensor axis is aligned with the target.

In certain configurations, the target is indicia on the outlet of the fluid source. The flow sensor may also include a follower and the base may further include a cam wherein the follower follows at least a portion of the cam when the flow sensor is mounted to the base. Optionally, the flow sensor further includes an opening and the base further includes a wedge-like protrusion wherein the opening is sized and shaped to accommodate a widest portion of the wedge-like protrusion and the optical sensor axis is aligned with the target when the widest portion enters the opening as the flow sensor is mounted to the base. The flow sensor may also include an opening and the base may further include a protrusion wherein the opening is sized and shaped to engage the protrusion and the cam is adapted to move the pin away from the protrusion while the protrusion enters the opening when the flow sensor is mounted to the base and when the follower is at a final position of the cam, the optical sensor axis is aligned with said target.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 10A is a side elevation view of a syringe compatible with a flow sensor system in accordance with an embodiment of the present invention.

FIG. 10B is an enlarged detail view of a portion of FIG. 10A as illustrated by Detail B.

FIG. 10C is a side elevation view of a tip label for a syringe compatible with a flow sensor system in accordance with an embodiment of the present invention.

FIG. 11A is a perspective view of a charger for a flow sensor system in accordance with an embodiment of the present invention.

FIG. 11B is an enlarged detail view of a portion of FIG. 11A rotated at a clockwise angle as illustrated by Detail C.

FIG. 11C is a top elevation view of a charger for a flow sensor system in accordance with an embodiment of the present invention.

FIG. 11D is a cross-sectional view taken along line X-X of FIG. 11C, with a base of a flow sensor system received within a portion of the charger, in accordance with an embodiment of the present invention.

FIG. 12 is a perspective view of a flow sensor and a mount in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
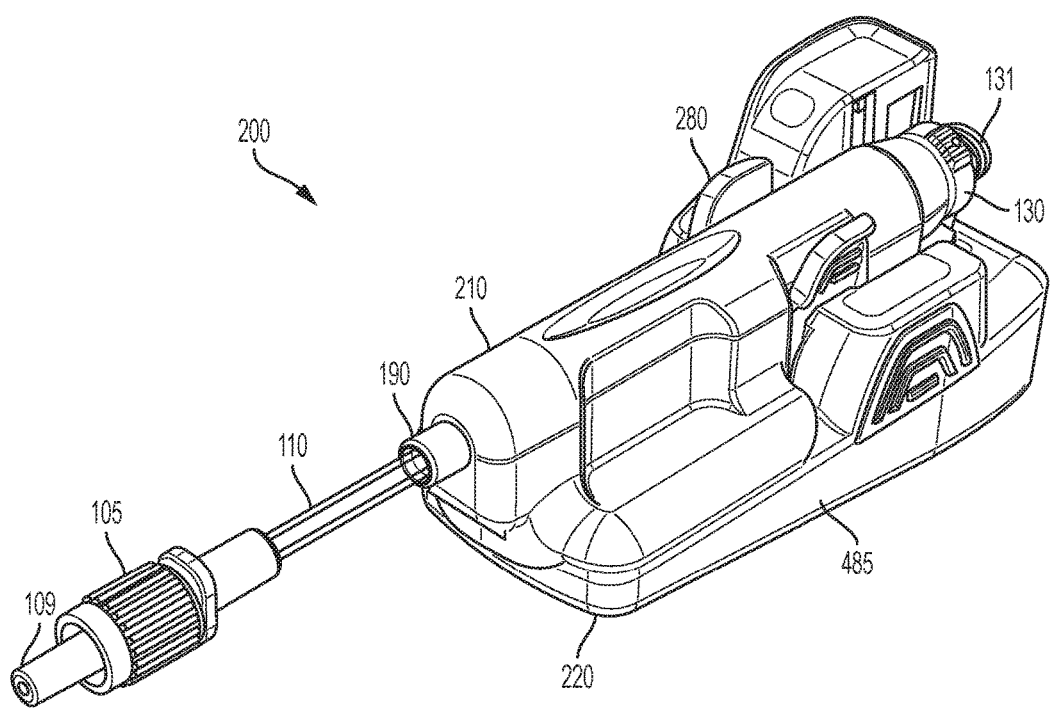
FIG. 1 is a distally-directed perspective view of a flow sensor system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

As used herein, proximal shall refer to a part or direction located away or furthest from a patient (upstream), while distal shall refer to a part or direction towards or located nearest to a patient (downstream). Also, a drug substance is used herein in an illustrative, non-limiting manner to refer to any substance injectable into the body of a patient for any purpose. Reference to a patient may be to any being, human or animal. Reference to a clinician may be to any person or thing giving treatment, e.g., a nurse, doctor, machine intelligence, caregiver, or even self-treatment.

FIGS. 1-12 illustrate an exemplary embodiment of a flow sensor system 200 of the present disclosure. Referring to FIGS. 1-12, a flow sensor system 200 of the present disclosure includes two main assemblies which fit together prior to use: a flow sensor 210 and a base 220. In one embodiment, the flow sensor 210 can be a single-use flow sensor which is engageable with reusable base 220. The flow sensor system 200 is an intelligent injection port. The flow sensor system 200 is attachable to an injection site ("Y Site" or stop cock, for example) for manually administered IV injections.

The flow sensor system 200 of the present disclosure can reduce medication error at bedside during bolus delivery. The flow sensor system 200 of the present disclosure can also provide a record of and electronically measure bolus delivery, which allows monitoring bolus delivery and automatic documentation of bolus delivery as part of a patient's health record. The flow sensor system 200 of the present disclosure can also provide alerts when bolus delivery inconsistent with a patient's medical record is about to occur.

Referring to FIGS. 1-5, in one embodiment, the base 220 is a non-sterile, reusable device that houses a battery, a scanner (either optical, mechanical, inductive, capacitive, proximity, or RFID), electronics, and wireless transmitter. In some embodiments, the base 220 is battery powered, and rechargeable. In some embodiments, each base 220 has a unique serial number imprinted on a surface of the base 220 or embedded therein that may be transmitted to a data system before use. The data system can be a local computer or tablet "Computer", a cellular phone, another medical device, or a Hospital Data System.

In one embodiment, the base 220 is removably connectable to the flow sensor 210. Referring to FIGS. 5A and 6-9, the base member 220 and the mechanical connection of the flow sensor 210 to the base member 220 is described. The base member 220 includes at least one deflectable wing tab 280 defining an opening for receiving at least a portion of the flow sensor 210 therein and for securing the flow sensor 210 within a portion of the base 220 prior to use. In one embodiment, a pair of wing tabs 280 secure the flow sensor 210 within the base 220. Optional gripping ribs 395 may be provided on an exterior profile for enabling a user to grasp the base portion 220.

Figure 6:
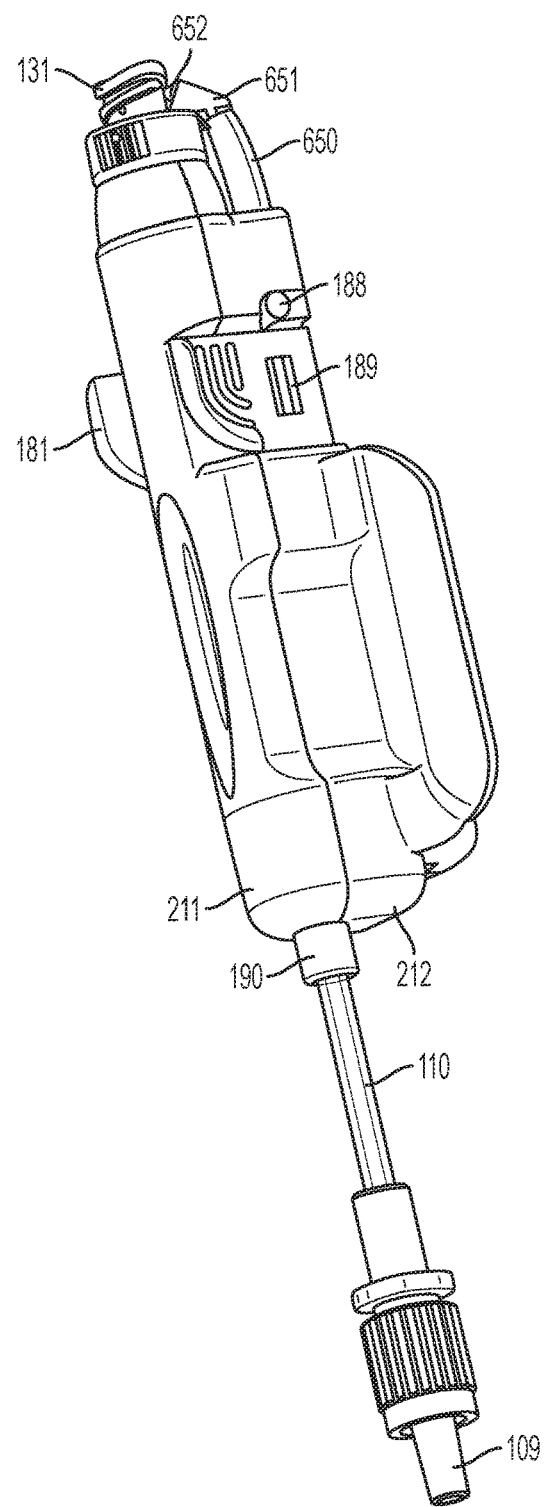
FIG. 6 is a perspective view of a flow sensor of a flow sensor system in accordance with an embodiment of the present invention.

An interior profile of the wing tab 280 may be provided with a catch 389 for corresponding engagement with a tab 189 provided on the flow sensor 210, as shown in FIG. 6, to restrain the flow sensor 210 within the base 220, as will be discussed further herein. The wing tabs 280 may be flexible to the extent that they may be outwardly deflected to allow for passage of the flow sensor 210 thereover. The interior of the wing tab 280 may be provided with a pin cam 388 which allows a pin 188 of the flow sensor 210, as shown in FIG. 7, to ride along such that the flow sensor 210 is moved proximally during assembly onto the base 220, to precisely align various optical and electrical components of the flow sensor 210 and the base member 220, as will be discussed further herein.

Referring to FIGS. 5B and 6-9, the base member 220 and the electrical connection of flow sensor 210 to the base member 220 is described. The base 220 includes an activation/engagement button 350 which allows for an indication that the flow sensor 210 has been engaged with the base 220.

In one embodiment, the activation/engagement button 350 signals to a microprocessor within the base 220 that a syringe has been properly engaged with the sensor 210 and its injection port 130.

Figure 7:
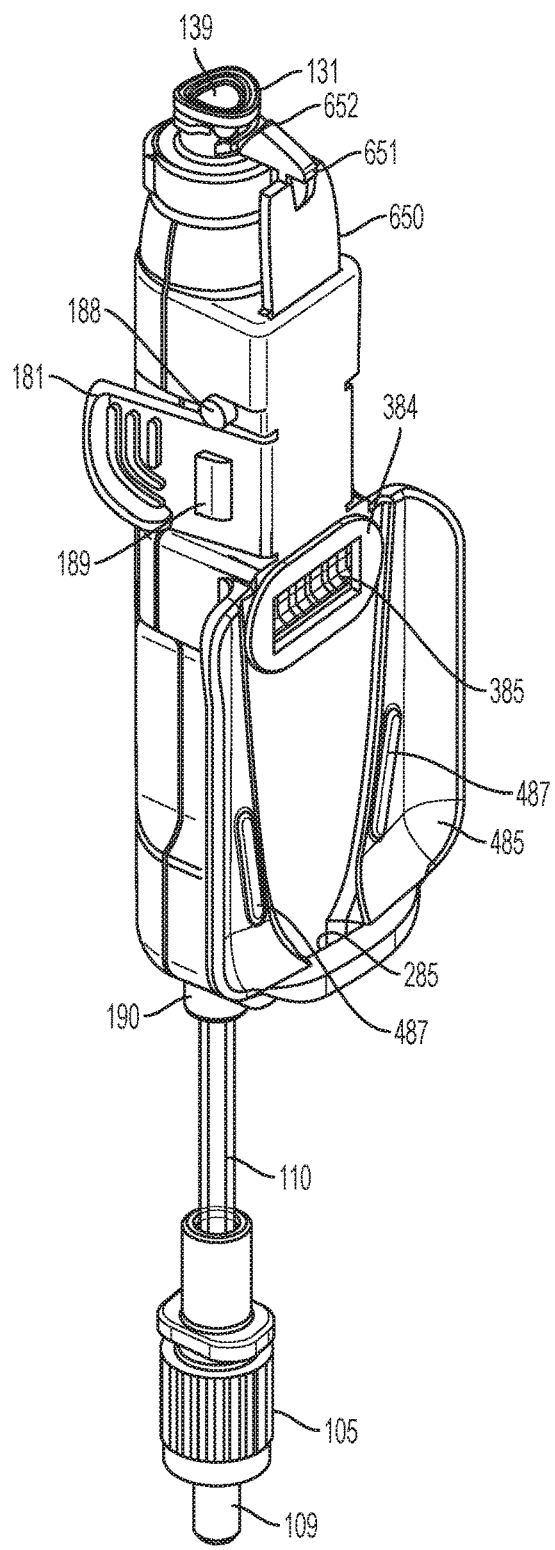
FIG. 7 is another perspective view of a flow sensor of a flow sensor system in accordance with an embodiment of the present invention.

The base 220 further includes a plurality of contacts 386 (FIG. 5B) for electrically engaging corresponding electrically active portions of the plurality of contact pins 385 (FIG. 7). A contour protrusion 488 surrounds at least a portion of the tongue 286. As shown in FIG. 7, a bottom surface of the sensor 200 includes a pin seal 384 surrounding a plurality of contact pins 385 to prevent contamination, thus minimizing electrical disruptions. In some embodiments the plurality of pins 385 comprise a four pin connector with two pins electrically connected to each piezo element 150, 151, as will be discussed further. In other embodiments, the plurality of pins 385 comprise a six pin connector with two pins electrically connected to each piezo element 150, 151 and two pins electrically connected to a battery (not shown) in the flow sensor 210.

The base member 220 further includes a tongue 286 surrounded by a shoulder 486 having a plurality of contacts 386 for electrically engaging corresponding electrically active portions of sensor 200 and a charger 900 (FIG. 11A), as will be discussed herein.

Referring to FIGS. 1-4B, 6-9, and 13, in one embodiment, the flow sensor 210 is a pre-sterilized disposable having an injection port 130 and a distal tubing connection, such as a Luer tip 109.

The flow sensor 210 may include a flow tube subassembly 10 consisting of a flow tube 100 having an outlet end 101 and an inlet end 102. The outlet end 101 may be provided in fluid communication with an outlet tubing 110 having an outlet connection 105 including a Luer tip 109 which may be optionally covered by a Luer cap 108. In a preferred embodiment, the outlet connection 105 is a plastic connector with a Luer tip 109, however, any suitable method to inject the medicament into a patient is envisaged to be within an aspect of an embodiment of the invention. For example, it may be desirable to replace the outlet connection 105 and tubing 110 with a needle for direct injection/infusion into a patient. Furthermore, it may be desirable to integrate the base 220 into a medication pen or infusion device for the delivery of insulin.

The inlet end 102 may be coupled to the reservoir of a medication pen or infusion reservoir. The inlet end 102 of the flow tube 100 may be provided in fluid communication with an injection port 130, and may optionally include a connection such as a threaded Luer lock 131 which is engageable with a source of a fluid to be injected. A pierceable septum 139 may be provided with the injection port 130 for maintaining sterility prior to use.

In a preferred embodiment, the injection port 130 is a plastic container with a split septum 139, however, any suitable method to inject the medicament through a flow sensor inlet 180 to a patient is envisaged to be within an embodiment of the present invention. For example, it may be desirable to replace the injection port 130 for direct connection to a medicament delivery device. In addition, it may be desirable to integrate the flow sensor inlet 180 to accept a direct fluidic connection to a medication delivery device.

In one embodiment, the flow tube 100 is comprised of a medical grade stainless steel and is approximately 50 mm long with a 1.0 mm inner diameter and a 1.6 mm outer diameter.

Figure 8:
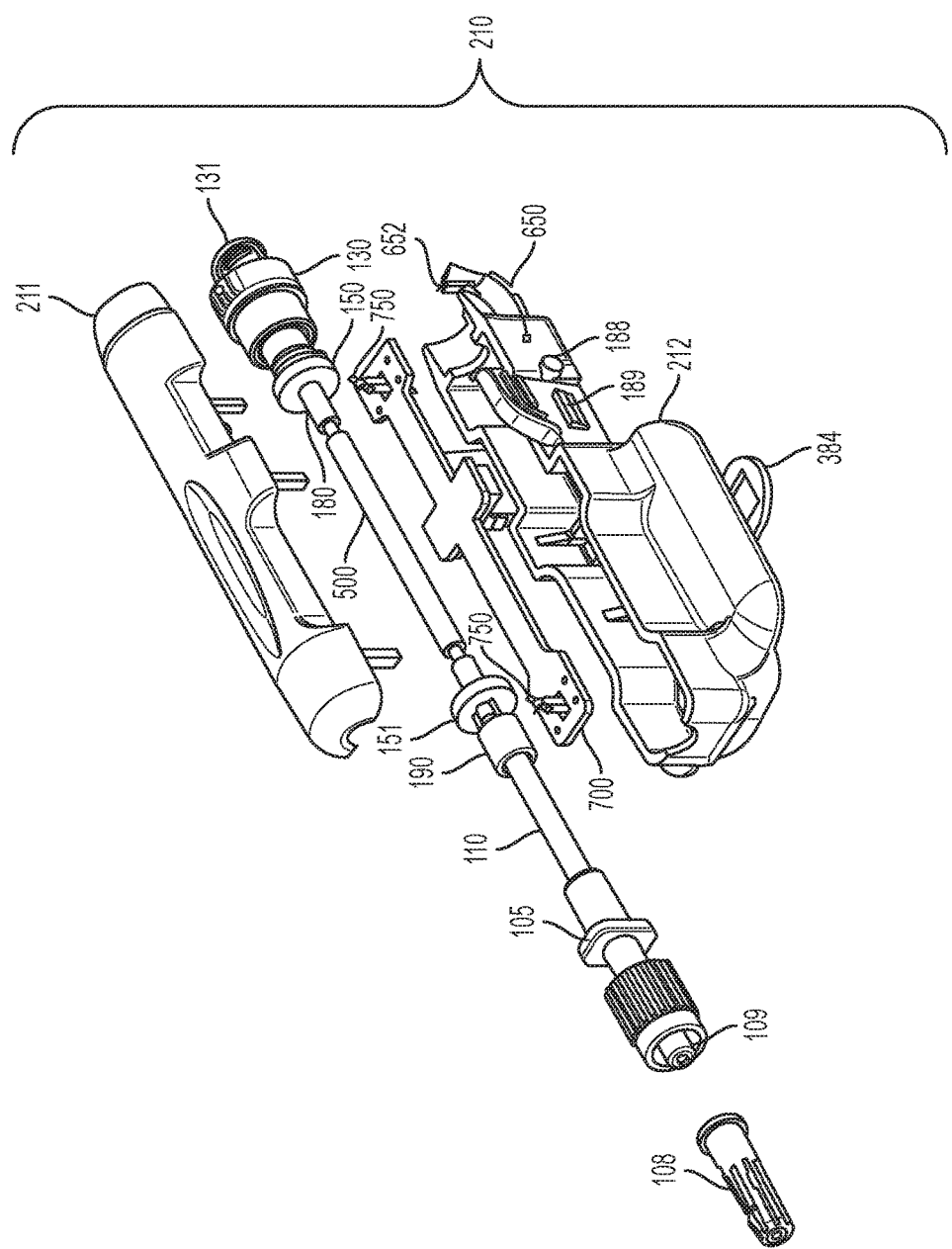
FIG. 8 is an exploded, perspective view of a flow sensor of a flow sensor system in accordance with an embodiment of the present invention.
Figure 9:
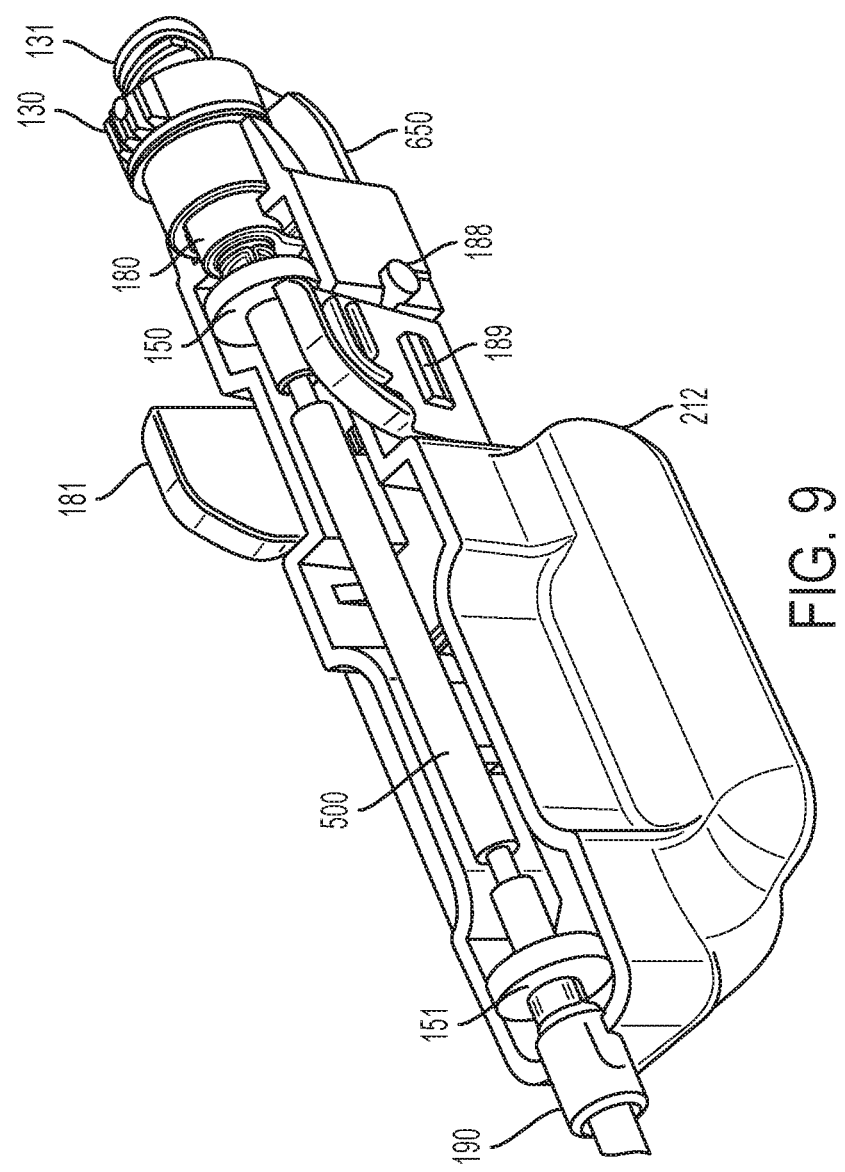
FIG. 9 is a perspective view of a flow sensor of a flow sensor system in accordance with an embodiment of the present invention.

The flow sensor 210 also includes a first piezo element or upstream transducer 150 and a second piezo element or downstream transducer 151. The first piezo element 150 may be provided with an inlet fitting 180, as shown in FIG. 8, for coupling with the injection port 130. Similarly, the second piezo element 151 may be provided with an outlet fitting 190, for coupling with the outlet tubing 110.

The flow sensor 210 can be supplied in a sterile package for a single patient use. In one embodiment, labeling is printed on the individual sterile package. In one embodiment, each flow sensor 210 has a unique serial number imprinted on a portion of its surface. In some embodiments, there are electronics in the flow sensor 210 which retain a unique identifier. These identifiers are transmitted either automatically or manually to a data system during use and data collection. In one embodiment, at the inlet end 102 of a flow sensor 210 the injection port 130 is a common needleless, Luer-Lok type. Typically, the inlet port or the injection port 130 is cleaned prior to giving an injection according to hospital policy. Additionally, flushing the flow sensor 210 with an IV fluid (e.g., normal saline syringe) is desirable before use. The injection port 130 on the flow sensor 210 typically supports up to 100 injections. In one embodiment, the flow sensor 210 has a male Luer-Lok connection, e.g., an outlet connection 105 having a luer tip 109, on a one-inch IV tubing pigtail at the outlet end 101. This male Luer-Lok connection may be attached to an IV line at a Y-site or IV manifold. Each flow sensor 210 has a unique serial number, however it may be desirable to only display a portion of the serial number on a portion of the exterior of the flow sensor 210. For example, the last 4 digits of the serial number may be imprinted on the surface next to its bar code. This human readable number is used to visually identify a flow sensor 210 within wireless range of communication of a computer. In some embodiments, the flow sensor 210 measures with an accuracy of ±5% for bolus volumes of 1.0 mL to 55 mL and ±20% for bolus volumes of 0.4 to 1.0 mL and has a dead-space volume of less than 0.3 mL.

Referring to FIGS. 11A-11D, in one embodiment, an optional separate charger 900 is compatible with the flow sensor system 200 and recharges a battery in the reusable base 220, if required, for reuse of the base 220. Referring to FIGS. 11A-11D, in one embodiment, the charger 900 includes a charger base 905 having an opening 925 for receiving the base 220, the opening 925 having charging pins 950 which engage corresponding contacts 386 in the reusable base 220. The charger 900 may include a sloped floor 930 for allowing disinfection liquid to drain therefrom. The device may also include elevated feet 999 to assist in drainage.

Reusable bases are typically supplied non-sterile and require disinfection and charging before use. It is preferred to disinfect each base 220 before first use. Typical commercial hospital disinfectants include alcohol-based quaternary ammonium, e.g., Metrex Research Cavi Wipes. In some embodiments, the base 220 can be used up to 500 times. Preferably, a rechargeable lithium ion battery is used within the base 220 and is not removable from the base 220. It is envisaged that a fully-charged base 220 will accommodate an entire patient case. In some embodiments, each base 220 is identified by labeling on the bottom of the device. Optionally, bases 220 are provided in individual boxes and each box is in a case package. The charger 900 may also include a power indicator 995. In one embodiment, when the base 220 is connected to a charger 900, up to four green light bars will illuminate on the top. The number of solid green light bars indicates the level of charge. A green blinking light on the base 220 will indicate it is recharging. In some embodiments, a useful life indicator is employed when the base 220 is connected to a charger 900 by use of a red light that indicates that the base 220 has exceeded its useful life. Optionally, on the Computer, an error message will display when a flow sensor system 200 whose useful life is completed is wirelessly connected to a tablet during patient setup. It would then be desirable to replace the base 220 with another and repeat the wireless connection to the Computer. Optionally, the flow sensor system 200 is provided in a mount which is an appliance that fits a standard Clarke socket to keep the flow sensor system 200 in place at the patient's bedside. Additionally, it may be desirable to clean and disinfect the charger 900 by using the procedure used for cleaning and disinfecting the base 220.

In one embodiment, the flow sensor system 200 supports injections using any Luer-lock type syringe. For example, referring to FIGS. 10A-10C, the flow sensor system 200 is compatible with a syringe 800 that is labeled. In one embodiment, the syringe 800 includes scale markings 805, a distal tip 810, a luer tip 815, a proximal end 820, a flange 825, a tip label 850 having human readable indicia 852 and machine readable indicia 854, a barrel label 860 having human readable indicia 862, and a plunger 890.

The base 220 of the flow sensor system 200 includes optics and a digital camera disposed within or behind a first window 360 (FIG. 2) capable of reading the machine readable indicia 854 provided on a label 850 of an encoded syringe. The first window 360 may be precisely aligned with Luer lock threads 131 present on the flow sensor 210 when the flow sensor 210 is assembled with the base 220, thus aligning the machine readable indicia 854 present on the label 850 on the syringe 800 during an injection cycle and/or medication determination cycle. The base 220 may further include a second window 370 (FIGS. 5A and 5B) having a light source for providing adequate lighting to the camera disposed within or behind window 360.

Additionally, the flow sensor system 200 is designed to work with encoded syringes that have a special barcode identifier on the Luer collar of the syringe, called "encoding". Preferably, encoded syringes include commercially-available drugs in prefilled syringes with a special barcode that stores information about the medication contained within the syringe. Encoded syringes are ready-to-use, passive, and disposable. The flow sensor system 200 also accommodates syringes not having encoding. The encoding syringes store the drug name and concentration contained within the syringe. Additional characteristics such as drug source, container size, drug manufacturer source, drug category color, among others, may also be included. When an encoded syringe is attached to the injection port 130 of the flow sensor 210, this barcode information is read by a scanner in the base 220 wirelessly transmitted by the flow sensor system 200 to the data system. Preferably, the 2-D barcodes will be added to syringes during the filling process.

In one embodiment, the flow sensor system 200 contains a device to capture and transmit an image of a 2-D barcode on the Luer collar of the syringe, and wirelessly transmit this image to a "Computer". Typically the Computer is a tablet computer communicating with multiple flow sensor systems 200. The 2-D barcode contains data, typically including the name and concentration of the drug in the syringe among other data. The Computer decodes this image, and displays and announces the drug attached. The barcode can contain the drug name and concentration. As the drug is injected, the flow sensor 210 in conjunction with the base 220 ultrasonically measures the volume of the injected drug and the time the drug was administered. This information may be stored in the flow sensor system 200 for later transmission to the Computer. The Computer uses this information to provide clinicians with an automated record of the drug name, concentration, volume, dose, and time of injection. The medication administration information is time stamped and displayed for clinical reference. Not all syringes used by the healthcare professional will contain a 2-D barcode. If a syringe without a 2-D barcode is inserted into the flow sensor system, the injection port 130, the flow sensor system 200 will prompt the user to manually enter the drug name and concentration into the computer. Information that is manually entered into the flow sensor system 200 is included in the patient medication record.

In one embodiment, the Computer can use a radio to wirelessly communicate with the flow sensor system 200 using an RF signal at 2.4 GHz to form a local medical device network. A number of flow sensor systems 200 and Computers may be used in the same vicinity such as a pre-operative care area or a post anesthesia care unit (PACU). Alert messages are communicated between the flow sensor system 200 and the Computer to advise the clinician of various operational characteristics of the flow sensor system 200. Some of these alerts inform the clinician of potential hazardous situations to allow user action to prevent harm to the patient or loss of medical data. Preferably, a lost wireless communication message will display when communication is lost between the flow sensor system 200 and the Computer. Preferably, all medication administration data from the flow sensor system 200 is transferred to the specific patient's medical record. In the event of a communication loss, medication administration data will be stored locally at the flow sensor system 200 and transferred to the Computer when communications are resumed.

The Computer may operate in a variety of modes. Typically the Computer has specialized flow sensor system 200 software for operations, a touch screen, and a wireless communications (Radio). It is typically mounted near an anesthetist or nursing work envelope and it may be removed for hand-held use. When the Computer is used in a hospital having a paper anesthesia record, the Computer supports features that assist with documenting the flow sheet portion and may help clinicians make the right decisions. In this configuration, the Computer complements the paper record-keeping activities by tracking and displaying injections given through the flow sensor system 200. The Computer also enables clinicians to manually document other pertinent IV drug injection and infusion information.

In one embodiment, the software screens follow a three-step approach consisting of: (1) connecting the flow sensor system 200 to the Computer; (2) setting up a patient's flow sensor system 200 for use; and (3) viewing medication administration in multiple views.

Figure 14A:
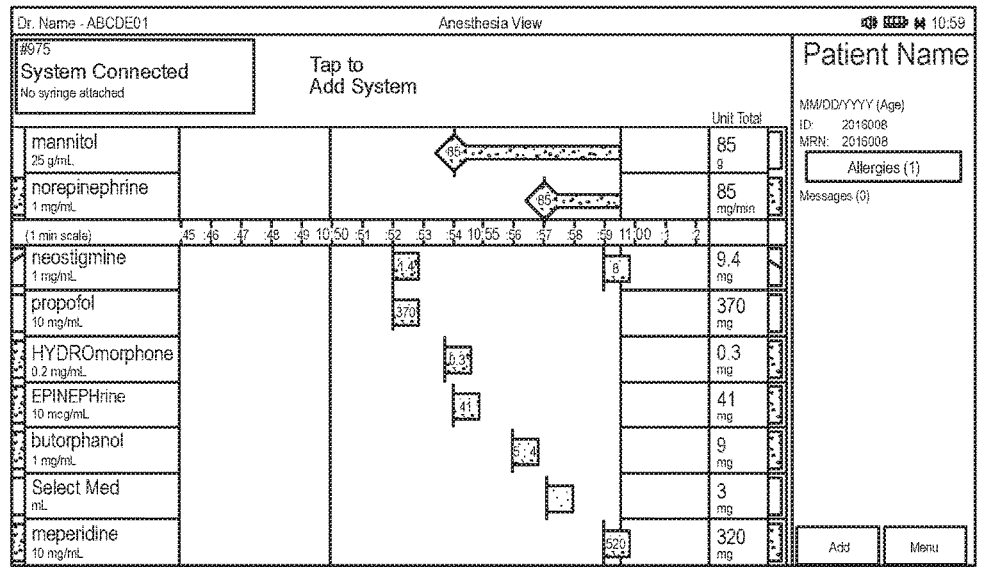
FIG. 14A is a schematic representation of a computer display in an anesthesia view in accordance with an embodiment of the present invention.

In some embodiments, a view on the computer displays anesthesia based information in an anesthesia view, as shown in FIG. 14A. Preferably, this view provides information about the patient and displays drug name/concentration and dose for a current injection as well as a historical list of medications that have been delivered to the patient since the current case was opened. It may also include a listing of infusions given to the patient, if the clinician recorded them on the Computer. In this view, up to three injection bars display across the top of the screen, one corresponding to each wirelessly connected flow sensor system 200. Each injection bar is a real time representation of the medication being administered through an individual flow sensor system 200. When an encoded syringe is attached to a single flow sensor system 200, the injection bar displays the drug name and concentration. When a non-encoded syringe is attached, the injection bar will prompt the clinician to identify the medication and concentration being delivered. As the medication is being delivered, the volume pushed (in mL) and the corresponding dose displays in real time in the injection bar on the Computer display.

A flow sensor system 200 of the present disclosure may also provide optional medication history. For example, as shown in FIG. 14A, the anesthesia view can include a historical list of medications delivered to the patient organized by the surgical care area (medications given in the transition time between care areas, will post to the next care area) arranged in a flow sheet format. Preferably, this view includes all medications that were administered to the patient since the flow sensor system 200 was activated with the more recent medication administrations preferably at the bottom of the list. A scroll bar is enabled when the list exceeds the visible space on the screen of the Computer. Preferably, when a new medication is added, the medication list scrolls automatically so the new medication name is visible. In the view, preferably a color tile corresponding to American Society for Testing and Materials International (ASTM) standards and endorsed by the American Society of Anesthesiologists displays to the left of the drug name. Optionally, a clinician may also specify that an admixture (mixed medication), or a diluted or reconstituted medication was delivered. Optionally, the Computer displays a case header which lists the patient name, date of birth, age in years, medical record number, and patient identification number. Optionally, the Computer will indicate that the patient has "no known allergies". Preferably, if the patient has allergies, that text is replaced by a button, more preferably, and the button has a number on the button that indicates the number of allergies.

Figure 14B:
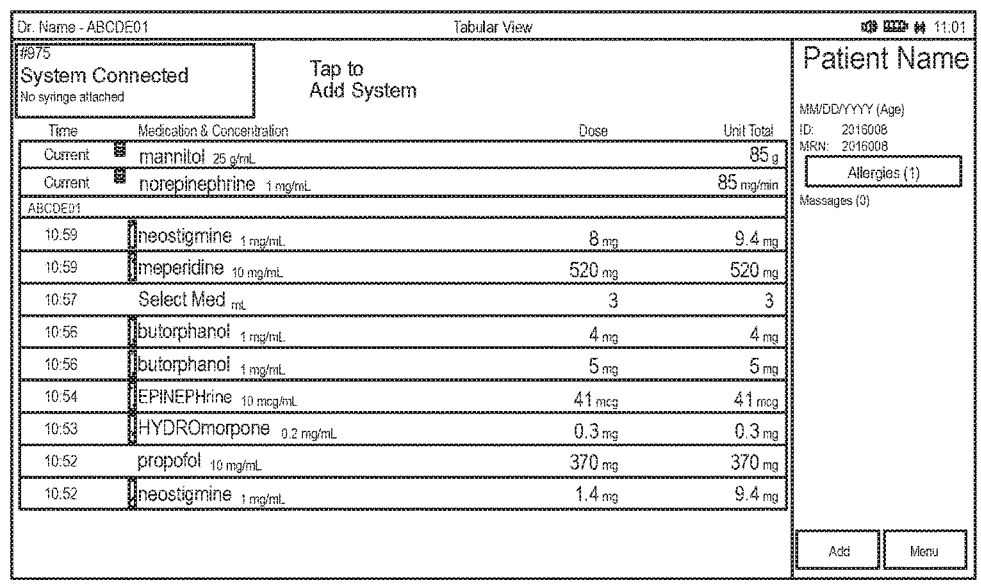
FIG. 14B is a schematic representation of a computer display in a tabular view in accordance with an embodiment of the present invention.

A flow sensor system 200 of the present disclosure may also provide an optional tabular view, as shown in FIG. 14B. For example, the tabular view is an alternate view for the clinician to interact with the flow sensor system 200. Similar to the anesthesia view described above, this view provides information about the patient and displays drug name/concentration and dose for a current injection as well as a historical list of medications that have been delivered to the patient. It may also include a listing of infusions given to the patient, if recorded by the clinician. The tabular view has many of the features of the anesthesia view; however, it is arranged in a tabular format. Preferably, the column headings in this view include time administered, medication with concentration, dose, and unit total. Optimally, the medications are displayed in reverse chronological order with most recent medication administered at the top of the list.

In one embodiment, the Computer provides two types of messages: (1) "Clinical" and (2) "System". Clinical messages are alerts and reminders that relate directly to an aspect of patient care delivery (e.g. contraindication or a reminder that it may be time to re-dose antibiotics). System messages provide status on relevant system operating parameters.

Messages provide instructions and a button for acknowledging or resolving. Messages display on the Computer until they are acknowledged or are no longer clinically relevant. Messages can be answered any time during a case. Prior to pausing or closing a case, the clinician is prompted to respond/answer unresolved medication messages generated during the case. An allergy alert illuminates the flow sensor system 200 and displays on the Computer when a clinician attaches an encoded syringe or selects a medication for a non-encoded syringe to which the patient has a known allergy. Optionally, this message may be overridden.

When dosing antibiotics, preferably the Computer tracks elapsed time since an antibiotic was last administered and displays and announces an antibiotic redosing message if the configured redosing interval has elapsed. The redosing interval is individual to each antibiotic, and it is configured in the drug library of the Computer or Gateway (further described below). In one embodiment, the flow sensor system 200 does not prevent or block the injection of a medication. In other embodiments, the flow sensor system 200 is able to block the injection of a medication.

In one embodiment, the Computer posts a message when the volume injected through the flow sensor system 200 was not measured. This may occur when the volume measured is outside of a range of sensing of the flow sensor system 200.

Optionally, the Computer wirelessly communicates bi-directionally with a software application that acts as a central hub to which all Computers (and thus multiple upon multiples of flow sensor systems 200) are connected, the "Gateway". Preferably, the Gateway is also connected to the hospital's other networked information systems. The Gateway allows all Computers to share patient case information such as drug name, dose, and time delivered with each other, and with the hospital's networked information systems. The Gateway also allows Computers to receive patient information such as patient drug allergies and patient drug orders from other networked hospital information systems.

Utilizing the flow sensor system 200 of the present disclosure encompasses the steps of connecting the flow sensor 210 to the patient's catheter or injection port (Y-site). Preferably, the flow sensor 210 and line is flushed. The flow sensor 210 is keyed to an individual patient using a unique serial number and the base 220 records medication administration through the port at the inlet end 102 of the flow sensor 210.

When a syringe 800 is attached to the injection port 130, the flow sensor system 200 identifies the medication and concentration for an encoded syringe by optically imaging and decoding a barcode on the Luer-Lok collar of the syringe 800. This information is wirelessly transmitted to the Computer. Preferably, the Computer displays and audibly announces the drug attached. The Computer also may perform allergy safety checks based on the patient's medical record.

In one embodiment, as the drug is injected, the flow sensor system 200 measures the volume dosed ultrasonically. The flow sensor system 200 wirelessly sends volume measurement information to the Computer. The Computer uses this information to provide clinicians with a medication administration record which is time stamped and displays for clinical reference during surgical procedures. Manually entered infusions and other information pertaining to non-encoded drug injections may be included in the patient medication record in the Computer and the Gateway. The Computer wirelessly communicates with the Gateway on the hospital network, and it may send medication administration to Hospital Information Systems, when configured, for reporting and electronic recordkeeping purposes. Preferably, the Computer wirelessly communicates with the existing Hospital Network using a standards based IEEE 802.11a/b/g/n enterprise WLAN network. The Gateway software and accompanied database will be a part of the hospital's enterprise information system. A number of Computers may be connected to the healthcare enterprise wireless network and to the intended Gateway software and database. Preferably, the Gateway and accompanied database provides a list of patients for the user to select and a formulary library of medications and fluids for injection or infusion. In one embodiment, actual medication and fluid administration data are sent to the Gateway and accompanied database for recordkeeping. Once recorded on the Gateway and accompanied database these data are preferably available in other care areas when the patient is transferred and the flow sensor system 200 is wirelessly connected to a Computer. Preferably, in the event of a communication loss, medication administration data will not be sent to the Gateway and therefore not available in the next care area.

Referring to FIGS. 1-12, use of a flow sensor system 200 of the present disclosure will now be described. First, preparing the flow sensor system 200 for an injection will be discussed.

In one embodiment, the flow sensor system 200 is prepared, attached to an IV line, and assembled for use. Preferably, there are pre-printed instructions located on the flow sensor 210 sterility pouch. First, a user obtains a flow sensor 210 in its sterile packaging and a fully-charged and disinfected reusable base 220. In one embodiment, a fully-charged base 220 has sufficient power for at least 24 hours of use under typical conditions. Optionally, the base 220 provides a visual indication of charge level via a display.

Next, the flow sensor 210 is flushed with sterile IV fluid before attaching to the Y-site. In one embodiment, the flow sensor 210 is flushed with more than 8 mL of sterile IV fluid. After flushing, a user can visually inspect the IV line for leaks, air, or blockage.

Figure 5A:
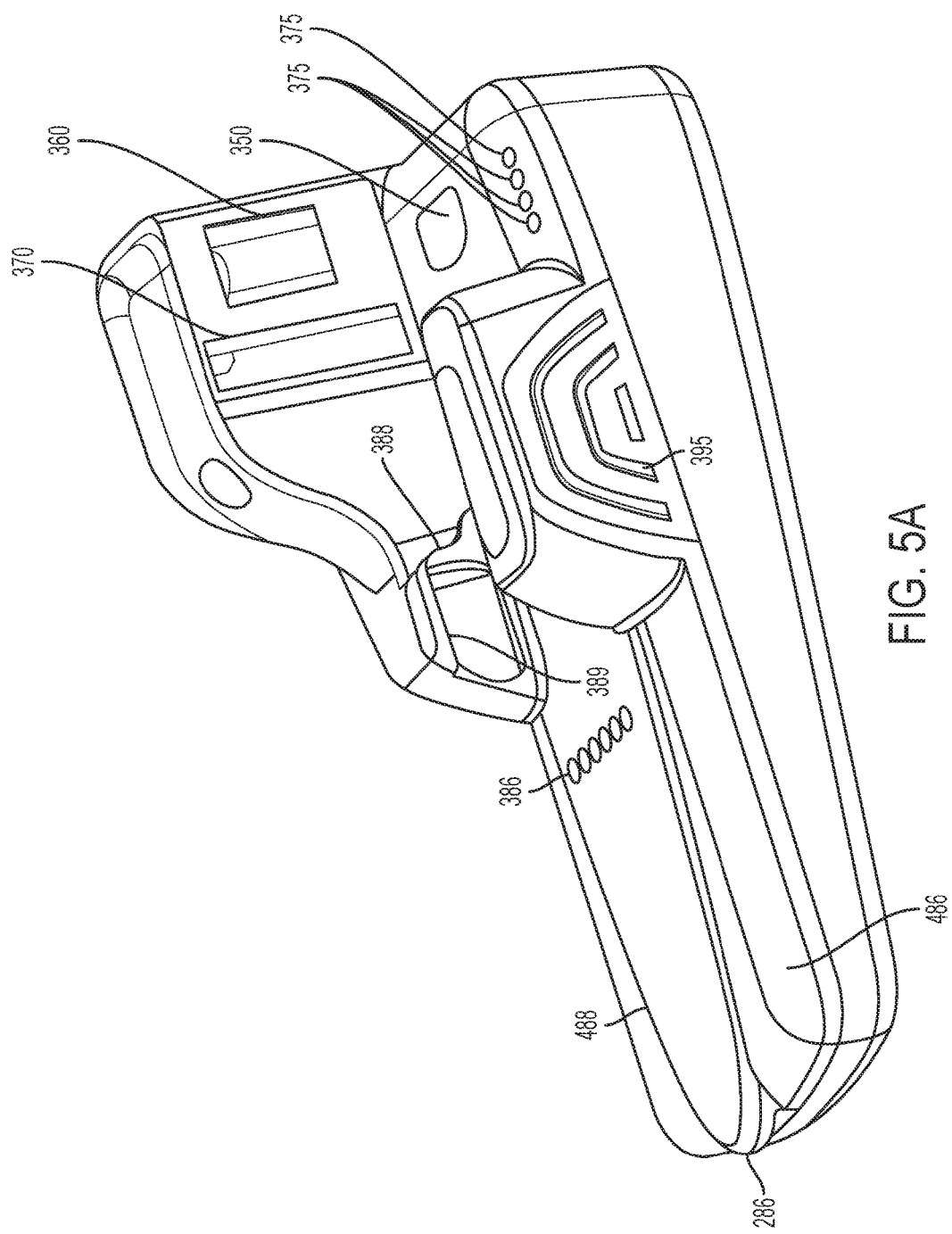
FIG. 5A is a perspective view of a base of a flow sensor system in accordance with an embodiment of the present invention.

Next, a user attaches the flow sensor 210 to the base 220 by joining the flow sensor 210 (tubing side) and base 220 front sections first, and then snapping the two together. Preferably, an audible snapping sound is heard to indicate a secure connection between the flow sensor 210 and the base 220. In one embodiment, connecting the flow sensor 210 to the base 220 automatically powers on the flow sensor system 200. In one embodiment, the connection of the flow sensor 210 to the base 220 is verified by a blinking light on the base 220. In other embodiments, other indicators may be used. Catch 389 of the base 220, shown in FIG. 5A, engages tab 189 of the flow sensor 210, shown in FIG. 6, to restrain the flow sensor 210 with the base 220 prior to initiation of an injection. In one embodiment, deflection of the wing tab or wing tabs 280 moves tab 189 with respect to catch 389 to initiate engagement or disengagement therewith. When the flow sensor 210 is assembled to the base 220, a cantilever 650 provided on the base 220, such as a lower housing 212 as will be discussed herein, is aligned with button 350 provided on the base 220. The interior of the wing tab 280 may also be provided with a pin cam 388 which allows pin 188 of the flow sensor 210, as shown in FIG. 6, to ride along such that the flow sensor 210 is moved proximally during assembly onto the base 220. During engagement, tongue 286 shown in FIG. 5A, is engaged within an opening 285 shown in FIG. 7. With continued reference to FIGS. 5A and 7, a vault 485 having ribs 487 on the flow sensor 210 as shown in FIG. 7, has a corresponding exterior profile taken with the shoulder 486 of the base 220, as shown in FIG. 5A, to engage for alignment of the first window 360 to precisely align with Luer lock threads 131 when the flow sensor 210 is assembled to the base 220. The vault 485 may provide a covering portion, such as a hollow cover, which forms a protective layer around the bottom portion of the base 220 to limit contamination, particularly to limit contamination of the pin seal 384 surrounding the plurality of contact pins 385. In one configuration, the vault 485 is a depending skirt that minimizes contact of the bottom of the base 220, such as the contact pins 385, and reduces contamination from from adhesive residue, blood spatter or other bodily fluids, dripping fluids from IV lines, and the like. In addition, the vault may allow for easier sterilization and cleaning for subsequent patient use.

In some embodiments, where appropriate, the flow sensor system 200 is secured to a surface in preparation for giving injections. For example, in some embodiments, referring to FIG. 12, a mount 1100 is used to secure the flow sensor system 200 to a surface. During this step, it is important to avoid kinks in the line between the flow sensor system 200 and IV line.

The flow sensor system 200 is now ready for delivery of IV medications. Preferably, any medications given through the flow sensor system 200 will be recorded in the electronic base 220 memory. In one embodiment, in the event of a flow sensor system 200 failure (excluding the IV fluid pathway), the flow sensor system 200 will still allow standard medication or fluid delivery through the port.

Figure 4A:
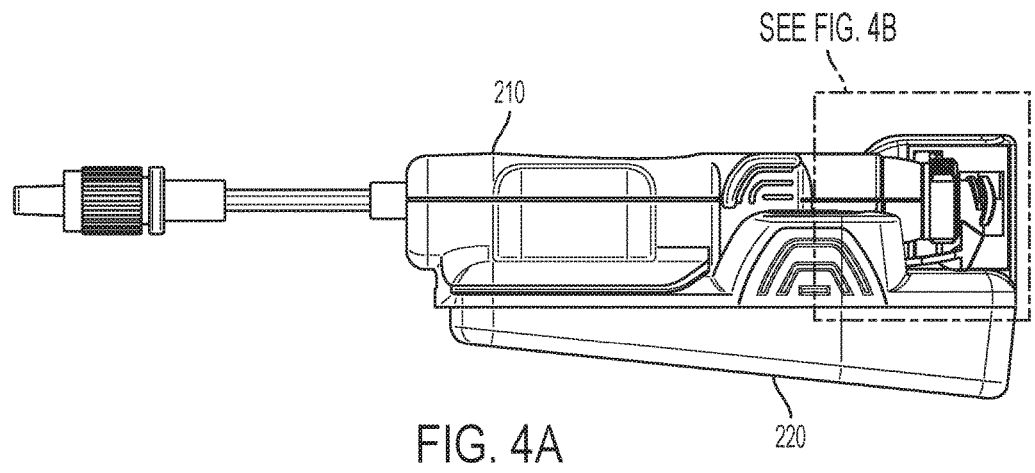
FIG. 4A is a side elevation view of a flow sensor system in accordance with an embodiment of the present invention.
Figure 4B:
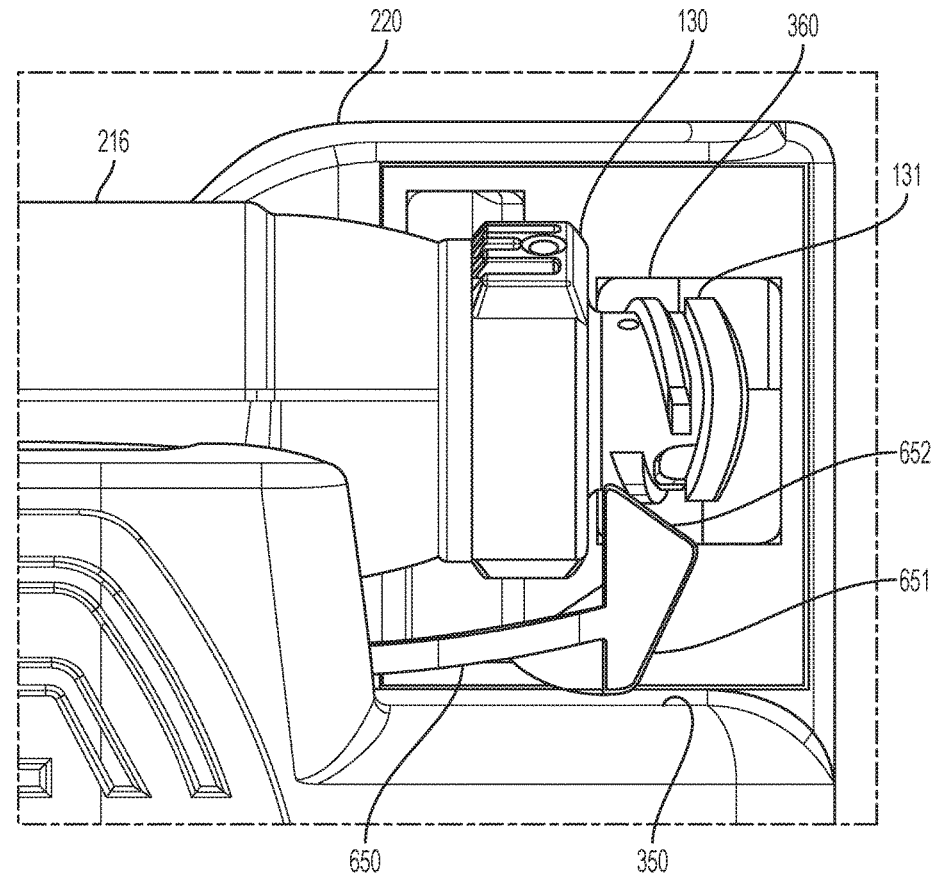
FIG. 4B is an enlarged detail view of a portion of FIG. 4A as illustrated by Detail A.

Next, giving an injection using the flow sensor system 200 will be discussed. First, the injection port 130 is cleaned by swabbing the hub according to normal hospital procedure. Next, a syringe 800 can be attached to the injection port 130 of the flow sensor 210 by completely turning the syringe 800 until the syringe 800 stops, i.e., a secure connection between the syringe 800 and the injection port 130 is made. Ideally, the caregiver double checks each medication name and concentration on the syringe 800 prior to attachment to the injection port 130 to assure the correct medication is given. During the injection cycle and/or medicament determination cycle, when syringe tip 810 contacts a syringe protrusion 652, as shown in FIG. 4B, the cantilever 650 is deflected radially from the longitudinal axis of the syringe 800. A pad protrusion 651 depresses button 350 on the base 220 and the button 350 signals the microprocessor to act.

Next, the drug and concentration displayed and announced by the Computer is verified as the intended drug and concentration. In one embodiment, the base 220 will alert the caregiver that an allergy is detected by an alert, for example, by flashing red, green, and yellow lights if a medication allergy is detected. Optionally, the Computer calculates a potential allergy reaction and provides an alert when any of these conditions is true: (1) an encoded syringe is inserted into the flow sensor 210 and the drug matches the patient's allergy profile; or (2) a non-encoded syringe is inserted into a flow sensor 210 and you select a drug from the select medication screen that matches the patient's allergy profile. If one of these conditions is true, the allergy alert flag on the Computer configuration is turned on.

In one embodiment, there is no check valve in the flow sensor 210, nor is one needed to use the flow sensor 210 safely and effectively. Typically, the flow sensor system 200 measures 0.4 mL to 55 mL per injection. If the injection flow rate is slow or a small volume is delivered (<0.4 mL) preferably an alert will display on the Computer. Optionally, an alarm is configured to detect rapid delivery from a large volume, e.g., 50 mL syringe. In this case, an alert is provided to check the dose.

In one embodiment an indicator 375, such as a series of four LED indicators, turn on in sequence to indicate to the user that fluid is moving through the flow sensor 210. When base 220 is mounted in the charger 900, the indicator 375 can indicate a level of battery charge of the base 220.

In one embodiment, it is preferred to follow all medication injections through the flow sensor system 200 with an encoded normal saline flush syringe to ensure the full dose of medications reaches the patient, especially when successively delivering two incompatible medications. Optionally, the flow sensor system 200 records such saline flush activity.

In one embodiment, injections are recorded whether or not the flow sensor system 200 is wirelessly connected to the Computer. The base 220 stores injection information in its memory and transmits this information upon wireless connection to the Computer.

In one embodiment, the Computer can accommodate multiple flow sensor systems 200 connected to one patient at a time. An additional flow sensor system 200 may be added at any time during a patient's treatment. When a flow sensor system 200 is connected to a Computer and there is no syringe attached to the flow sensor 210, the active injection bar reads "Sensor Connected, No syringe". On the Computer display, a battery status icon in the upper right corner of the injection bar indicates the battery charge level of the base 220 to which the flow sensor 210 is connected. For each injection a caregiver may enter a comment on the Computer.

The present disclosure provides a flow sensor sub-assembly for sensing flow of a fluidic medicament. The flow sensor sub-assembly includes a first spring contact and a second spring contact. In one embodiment, the spring contacts are secured to a base that has a circuit for conducting an electrical signal to and from the spring contacts to a microprocessor. The first spring contact is in electrical communication with a first piezo element and the second spring contact is in electrical communication with a second piezo element. The first spring contact has a first contact force against the first piezo element and the second spring contact has a second contact force against the second piezo element, and the first contact force is equivalent to the second contact force. The present disclosure also provides a circuit board for interfacing to a flow sensor having a plurality of piezo elements for transmitting a flow signal indicative of flow of a fluidic medicament.

A spring contact of the present disclosure provides electrical contact to a piezo element. For example, a spring contact of the present disclosure provides electrical contact to a silvered surface of a piezoelectric crystal. Furthermore this contact provides a spring force selected to accommodate assembly tolerances, temperature variation, electrical requirements, material selection for a long life to silver, and assembly features for a single-sided printed circuit board assembly (PCBA) attachment. The flow sensor sub-assembly of the present disclosure provides for four contacts used in a sensor to have the same force on both surfaces of each of two piezo elements, such as crystals, in a single transducer.

A circuit board of the present disclosure provides a single-sided PCBA. The single-sided PCBA of the present disclosure provides a lower cost design than conventional double-sided PCBA designs. The circuit board of the present disclosure also provides a means to maintain mechanical loading of the crystal contacts when the transducer is inserted to the PCBA.

Electrical contacts to the ultrasound crystal have previously been accomplished by soldering wires to a silver coating. A spring contact of the present disclosure provides a cost reduction method by using the spring contacts to connect to the crystal. In particular, a single-sided printed circuit board (PCB) of the present disclosure provides for a lower cost design and a through hole contact design. The design of the present disclosure includes the force exertion by the spring constant, dimension of separation between contacts, material type of the springs, the range of forces necessary, and tolerance control of forces exerted by the spring contact, which are all important to eliminate soldering. If soldering is too hot, it often takes silver off the surface of the crystal. Another problem with soldering is leaving too much solder behind, which may also cause loading of the ultrasonic physical characteristics. Consistent electrical and physical contact (repeatability) for both crystals is important as well as sensor to sensor calibration. The forces cannot be too high (potential for a slurry to develop) or too low (variable impedance).

The flow sensor sub-assembly of the present disclosure provides a high volume, disposable design with benefits for its cost, reliability, and repeatability. The flow sensor sub-assembly of the present disclosure allows for future automation features. The flow sensor sub-assembly of the present disclosure provides for maximal tolerance designed in conditions. The flow sensor sub-assembly of the present disclosure is able to fit inside the housing of a flow sensor 210.

Figure 13:
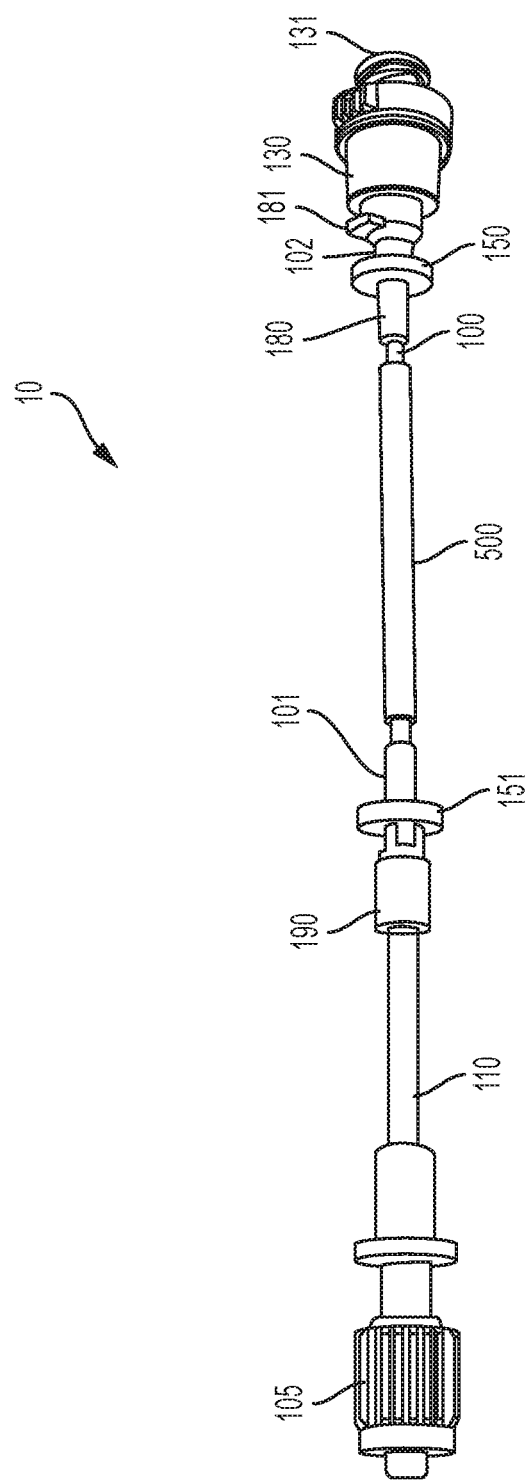
FIG. 13 is a perspective view of a flow tube sub-assembly in accordance with an embodiment of the present invention.
Figure 15:
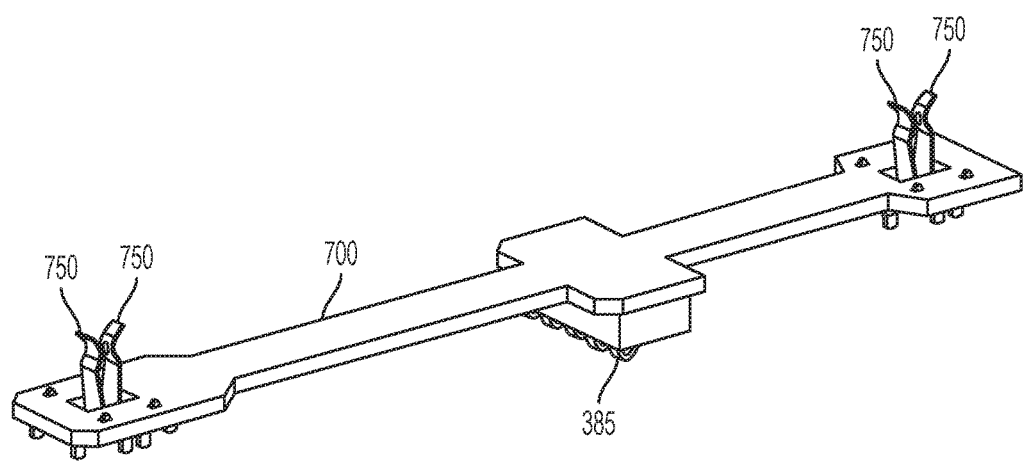
FIG. 15 is a perspective view of a circuit board in accordance with an embodiment of the present invention.
Figure 16:
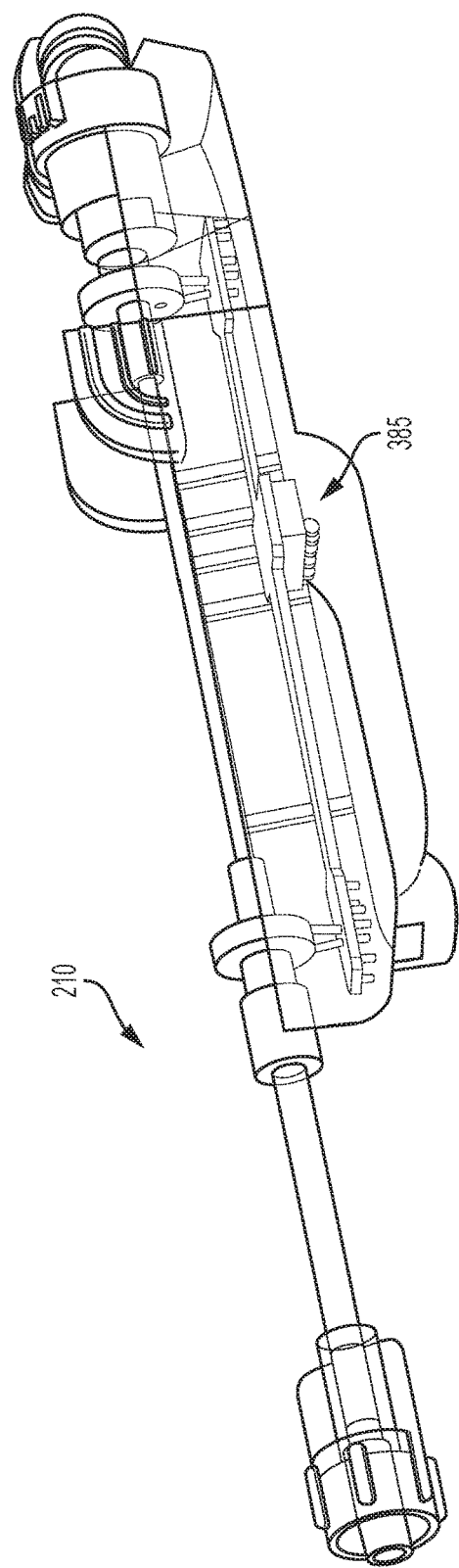
FIG. 16 is a perspective view of a flow sensor in accordance with an embodiment of the present invention.
Figure 17A:
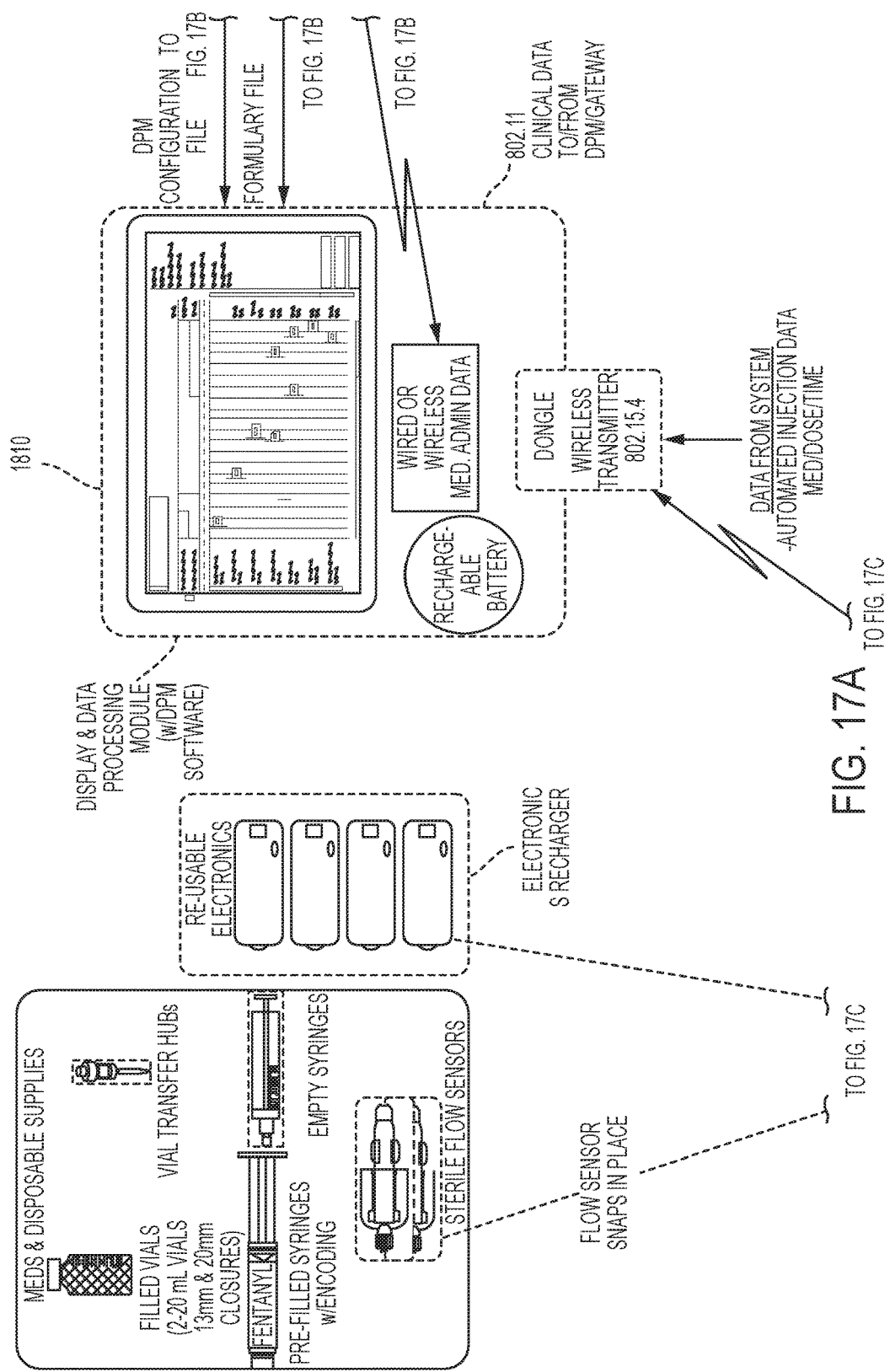
FIG. 17A-C are block diagrams of a flow sensor system in accordance with an embodiment of the present invention.
Figure 17B:
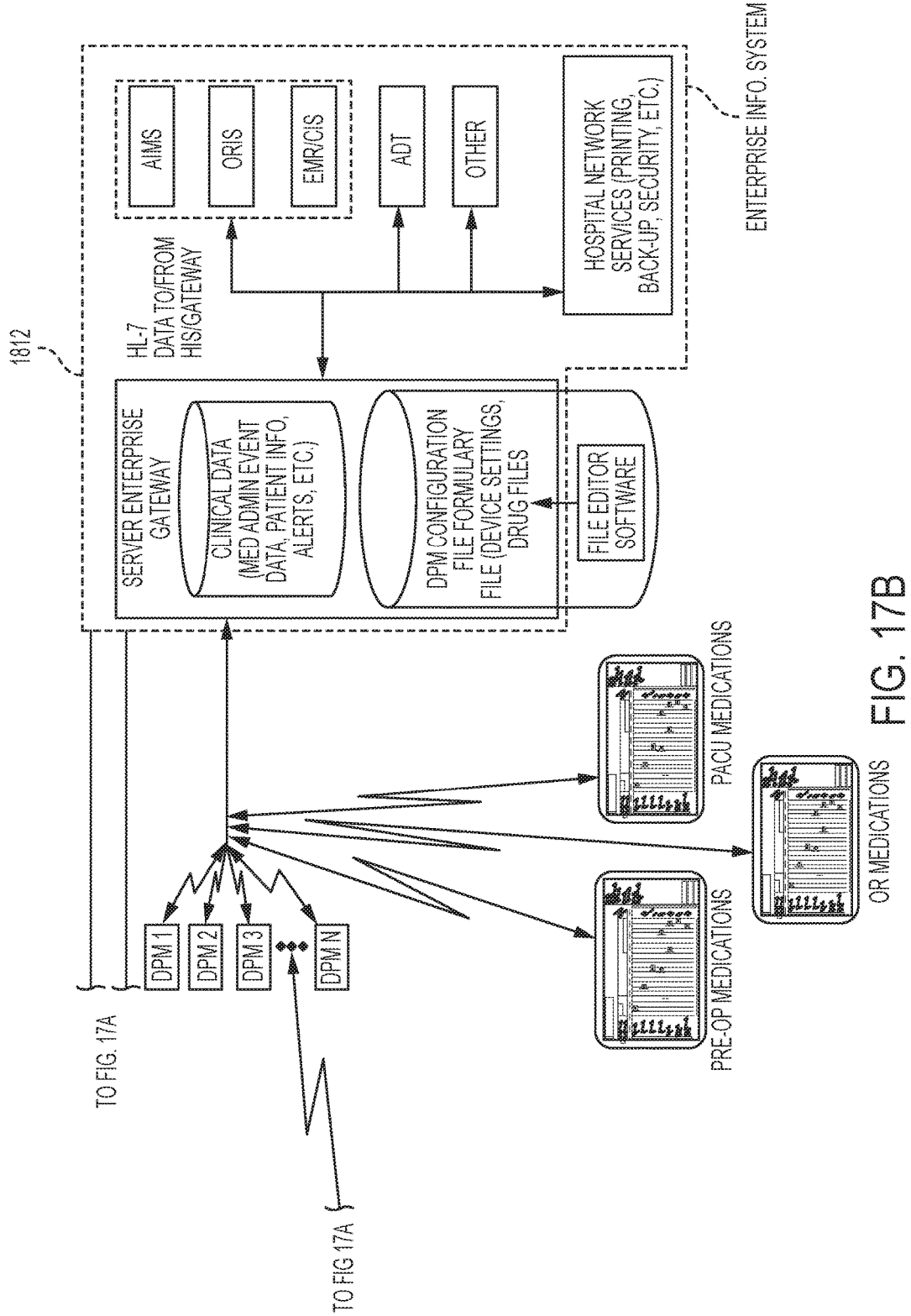
Figure 17C:
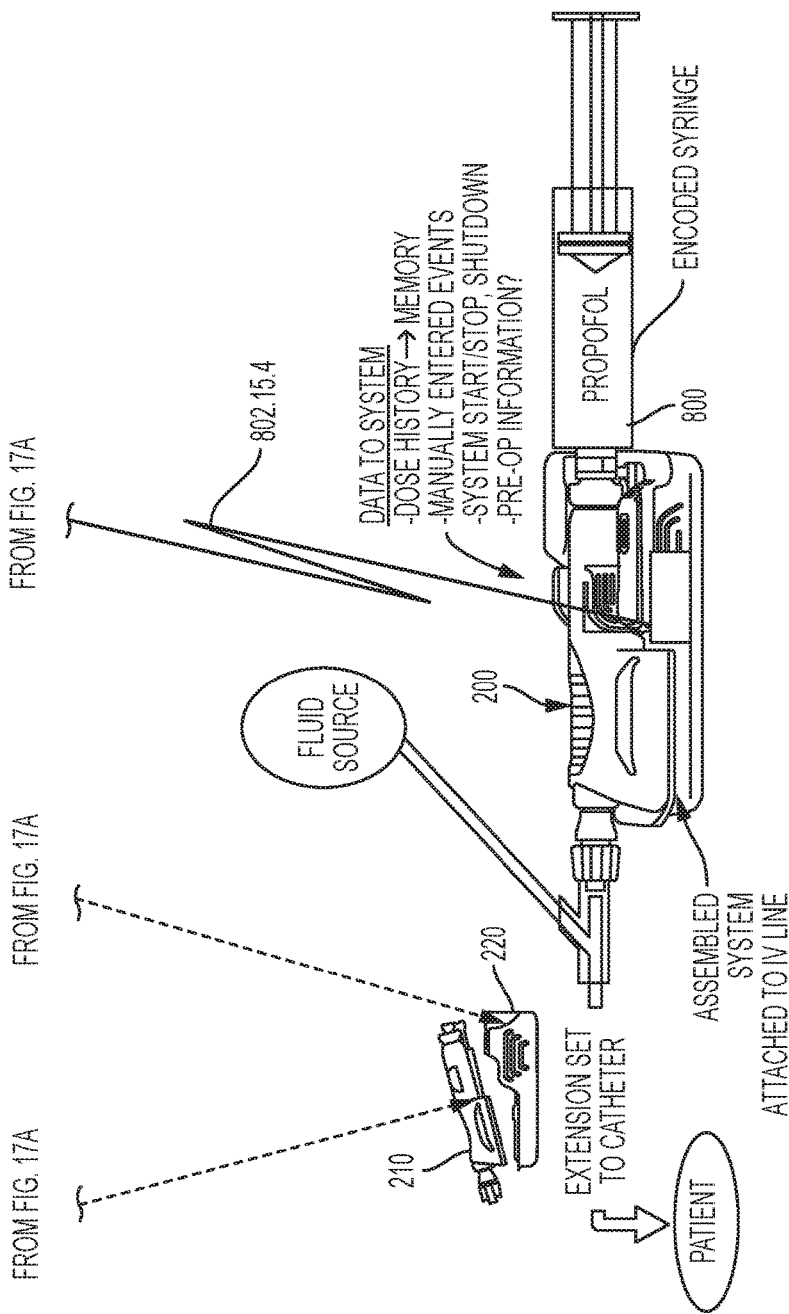
Figure 18A:
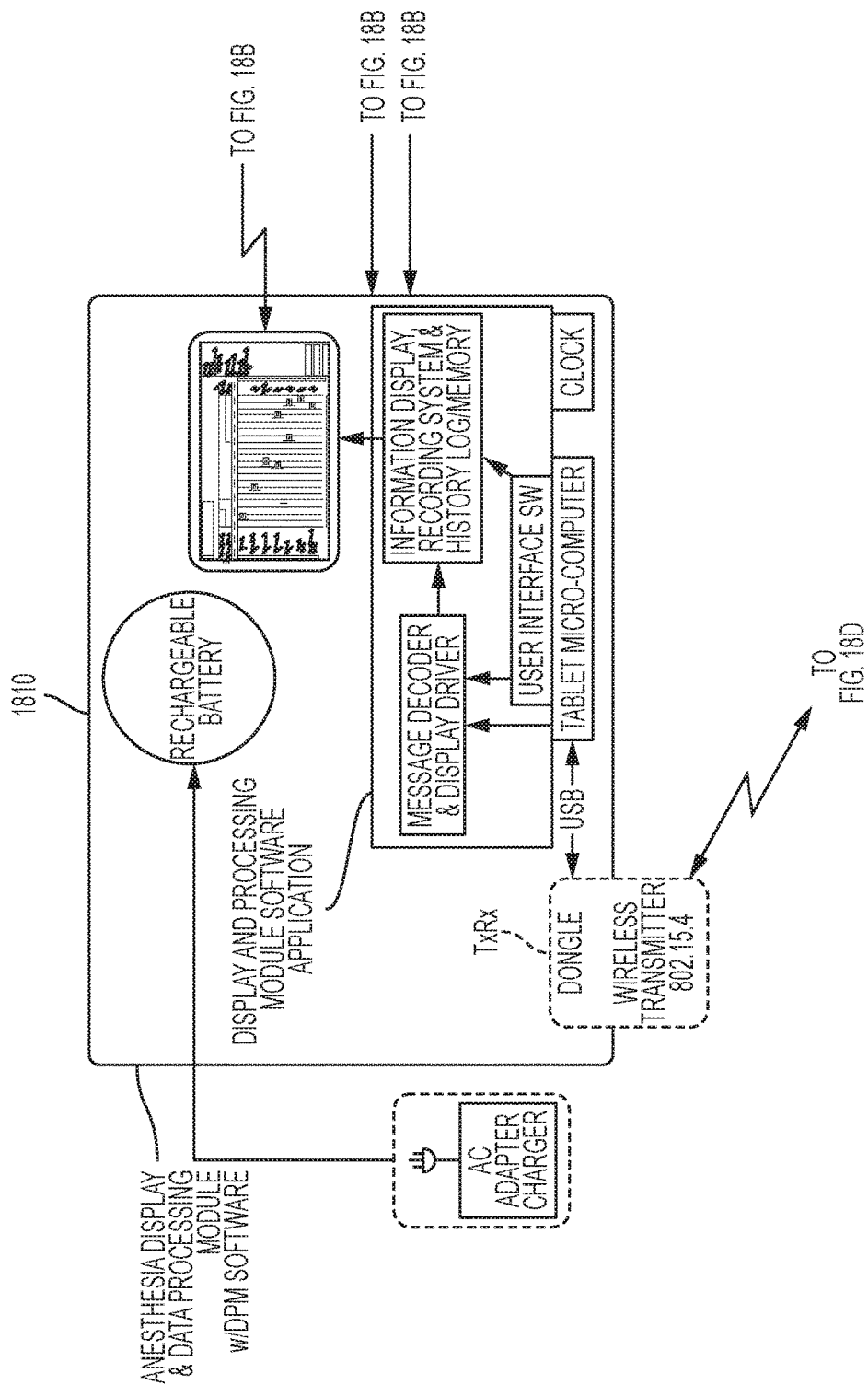
FIG. 18A-D are block diagrams of a flow sensor system in accordance with an embodiment of the present invention.
Figure 18B:
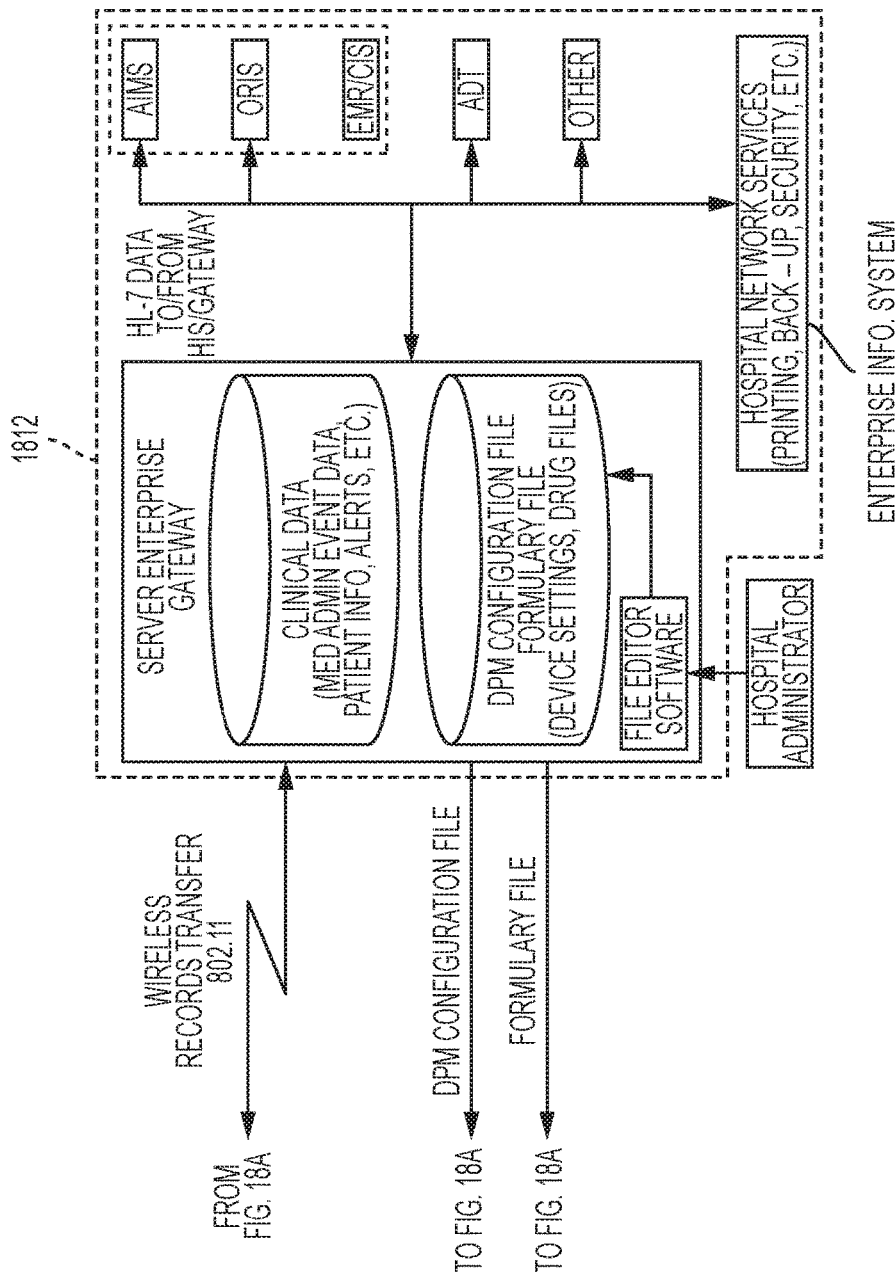
Figure 18C:
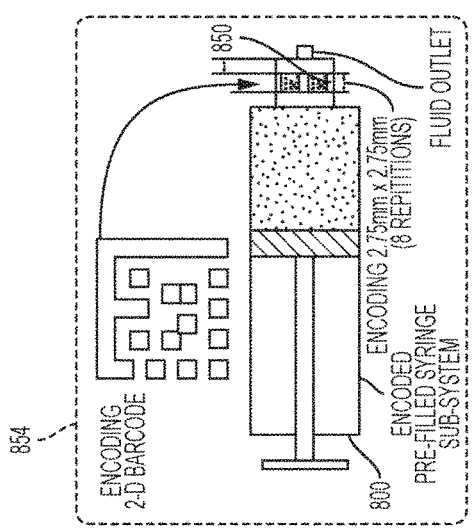
Figure 18D:
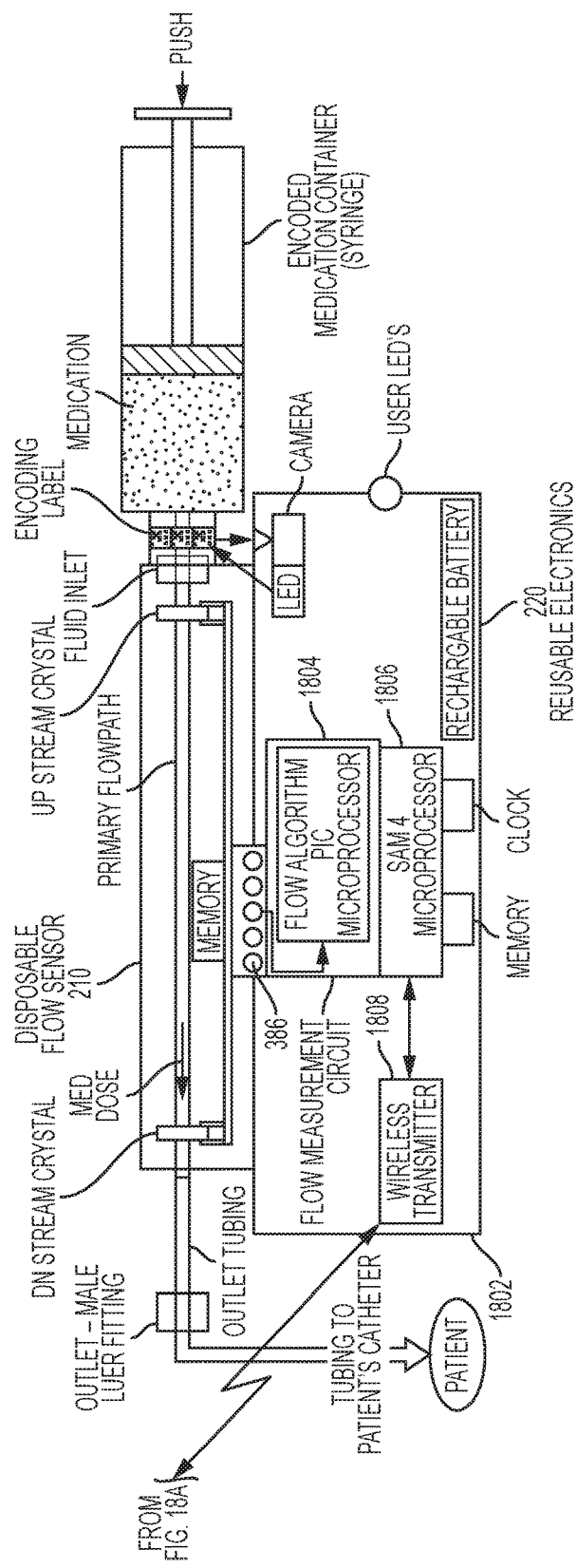

Referring to FIGS. 8, 13, and 15, a sub-assembly 10 for a flow sensor 210 for sensing flow of a fluidic medicament generally includes a flow tube 100 having a flow tube inlet 102 and a flow tube outlet 101, through which a medicament flows, a first piezo element 150 arranged at an upstream position of the flow tube 100 and a second piezo element 151 arranged at a downstream position of the flow tube 100, a first spring contact 750, and a second spring contact 750. In one configuration, the sub-assembly 10 for a flow sensor 210 may be utilized as a flow sensor 210 and inserted into the base 220, where contacts 750 are integrated into the base 220 rather than as a component of a housing 211, 212 of the flow sensor 210. Preferably, the upstream transducer 150 and downstream transducer 151 are interchangeable, however, it is envisaged that they may be purposefully constructed for their respective positions on the flow sensor sub-assembly 10.

In one embodiment, the first piezo element 150 and the second piezo element 151 are mounted apart a pre-selected distance from each other. In one embodiment, each of the spring contacts 750 are secured to a base, e.g., a circuit board 700. The circuit board 700 includes a circuit for conducting an electrical signal to and from the spring contacts 750 to a microprocessor. The first spring contact 750 is in electrical communication with the first piezo element 150 and the second spring contact 750 is in electrical communication with the second piezo element 151. The first spring contact 750 has a first contact force against the first piezo element 150 and the second spring contact 750 has a second contact force against the second piezo element 151. In one embodiment, the first contact force is equivalent to the second contact force. In another embodiment, circuit board 700 can contain a non-volatile memory containing the serial number of the sensor 210, calibration data and/or flow calculation constants for communication to the electronic microprocessor of the base 220.

In one embodiment, the flow tube 100 includes an inner flow tube 100 and end fittings, e.g., an inlet fitting 180 at an inlet end 102 and an outlet fitting 190 at an outlet end 101, for securing the inner flow tube to the respective end fittings 180, 190. In one embodiment, the first and second piezo elements 150, 151 are mounted to the end fittings 180, 190.

In one embodiment, the circuit is formed integrally with a flow sensor housing by injection molding. In one embodiment, referring to FIG. 8, the assembly may include a flow sensor upper housing 211 engageable with a flow sensor lower housing 212 about the flow sensor 210. In one embodiment, the first piezo element 150 and the second piezo element 151 are annular in shape and encircle the flow tube 100 at each respective mounting point.

Referring to FIGS. 1-9, 13, and 15, in one embodiment, the flow sensor 210 sub-assembly of the present disclosure is contained within a flow sensor housing 211, 212. A portion of the flow sensor housing 212 is coupled to a flow sensor base 220 which contains a microprocessor and a circuit that includes connecting pins for providing an electrical signal from the flow sensor 210 sub-assembly to the microprocessor within the flow sensor base 220.

In some embodiments, the flow sensor 210 sub-assembly is disposed after the flow sensor 210 sub-assembly is used to sense the flow of at least one fluidic medicament. In some embodiments, the flow sensor base 220 is reusable and is usable with different flow sensor 210 sub-assemblies.

Referring to FIGS. 8, 13, and 15, a circuit board 700 of the present disclosure for interfacing to a flow sensor 210 that includes piezo elements 150, 151 for transmitting a flow signal indicative of a flow of a fluidic medicament includes a base or circuit board 700, a first pair of spring contacts 750, a second pair of spring contacts 750, and a plurality of pins 385 in electrical contact with a plurality of electrical circuit traces. In one embodiment, the circuit board 700 includes a plurality of electrical circuit traces having a first end and a second end.

Referring to FIGS. 8 and 15, the first pair of spring contacts 750 for bias and electrical interface with a first piezo element 150 are mounted to a first end of the circuit board 700 and are in electrical communication with at least one electrical circuit trace. Also, the second pair of spring contacts 750 for bias and electrical interface with a second piezo element 151 are mounted to a second end of the circuit board 700 and are in electrical communication with at least one electrical circuit trace. The plurality of pins 385 are in electrical contact with the plurality of electrical circuit traces and configured to form electrical contacts with the plurality of contacts 386. In one embodiment, each of the spring contacts 750 are pre-configured such that the bias against the first piezo element 150 and the bias against the second piezo element 151 are equivalent and the electrical circuit traces are configured such that each of the pins and contacts 385, 386 are in electrical communication with a single spring contact 750.

In one embodiment, the circuit board 700 is formed integrally with a flow sensor housing 211, 212 by injection molding. The circuit board 700 may be assembled into a flow sensor housing 211, 212 in at least two orientations and provides transmission of a flow signal from the piezo elements 150, 151 to a microprocessor. In one embodiment, the circuit board 700 is disposed of after a flow sensor 210 is used to sense the flow of at least one fluidic medicament. Advantageously, after a flow sensor 210 is used to sense the flow of at least one fluidic medicament, the circuit board 700 is usable with a different flow sensor 210.

Referring to FIGS. 1, 5A, 5B, 7, and 15-18, a cross-component electrical circuit is formed by the plurality of pins 385 engaging the plurality of contacts 386 when the flow sensor 210 is mounted onto the base 220. As described herein, the pins 385 are in electrical communication with the piezo elements 150, 151 and/or an internal controller and memory of the flow sensor 210. The contacts 386 are in electrical communication with a controller circuitry 1802 in the base 220. The cross-component electrical circuit enables electrical communication between the flow sensor 210 and the base 220. For example, the flow sensor 210 can send signals from the piezo elements 150, 151 representing characteristics or attributes of the flow of the medicament in the flow tube 100 via the cross-component electrical circuit formed by the connection between the pins 385 and the contacts 386 to the controller circuitry 1802 in the base 220.

The controller circuitry 1802 comprises a flow measurement circuit 1804 including hardware, such as a microprocessor and/or software configured to execute a flow algorithm to analyze the flow of the fluidic medicament based on the characteristics or attributes of the fluid flow, e.g., fluid type, flow rate, dose time, etc., received from the flow sensor 210, a microprocessor 1806, such as a SAM 4 microprocessor including memory and a clock, configured to control the flow measurement circuit 1804, and a wireless transmitter 1808 configured to be controlled by the microprocessor 1806 to communicate with one or more external computing devices. Although FIGS. 16 and 17A-C are described mainly with respect to wireless communications between elements therein, in some embodiments the wireless communications and connections can be wired communications and connections.

Figure 2:
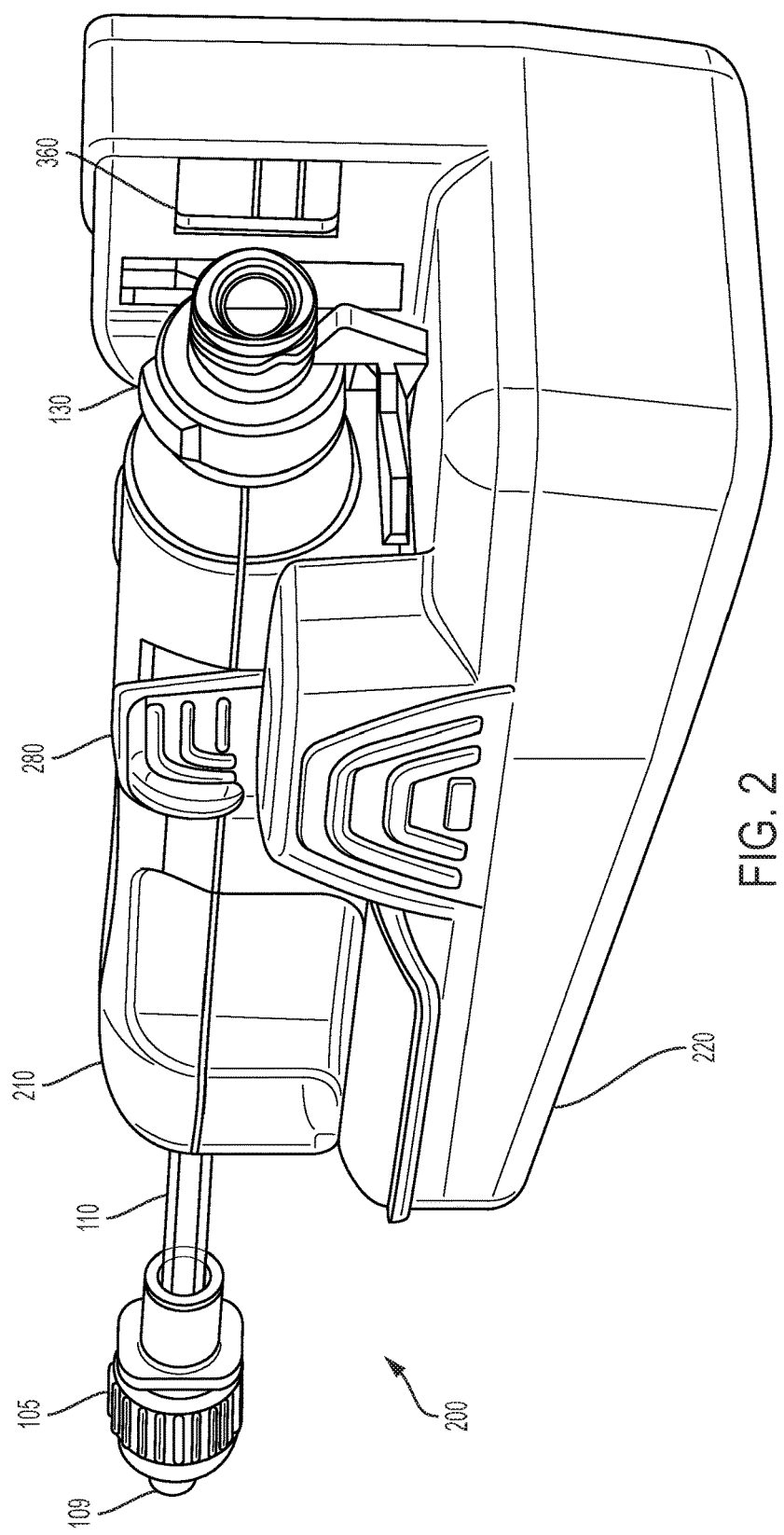
FIG. 2 is a proximally-directed perspective view of a flow sensor system in accordance with an embodiment of the present invention.
Figure 3A:
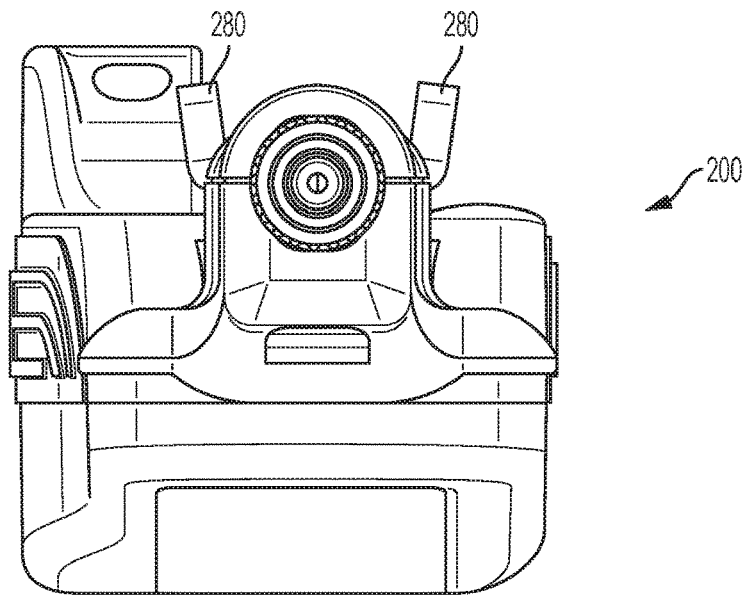
FIG. 3A is a proximal elevation view of a flow sensor system in accordance with an embodiment of the present invention.
Figure 3B:
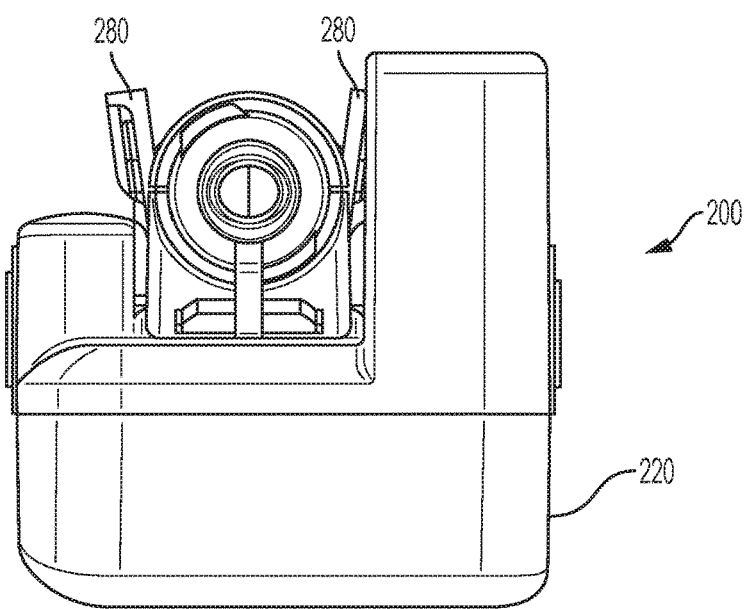
FIG. 3B is a distal elevation view of a flow sensor system in accordance with an embodiment of the present invention.
Figure 5B:
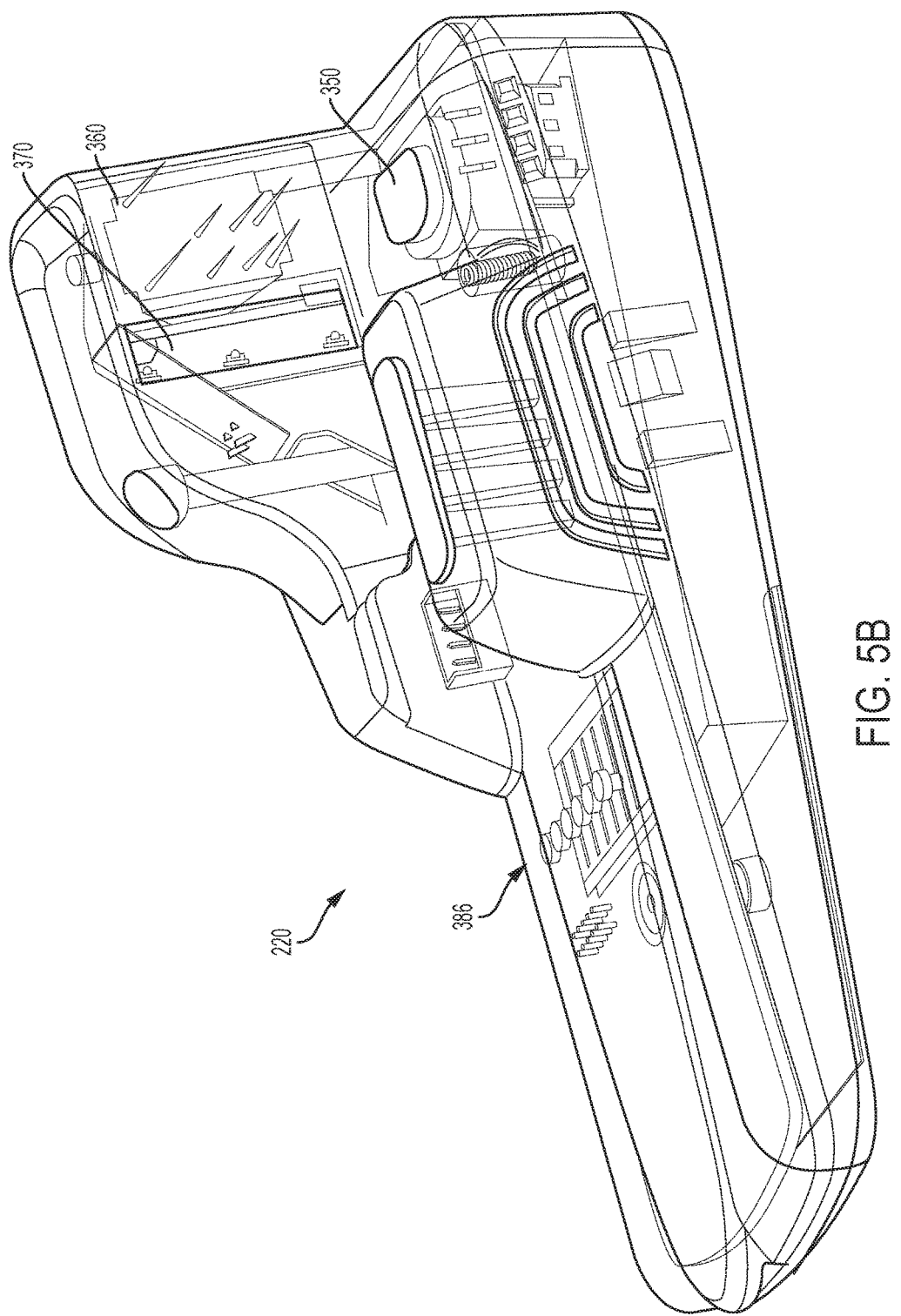
FIG. 5B is a perspective view of the base of FIG. 5A illustrating the optical and electrical components.

The controller circuitry 1802 is configured to generate an operation modification signal in response to one or more characteristics or attributes of the fluid flow matching one or more conditions specified by one or more rules. For example, the controller circuitry 1802 can execute the flow algorithm based on data representing characteristics or attributes of the fluid flow received from the piezo elements 150, 151 and/or the digital camera disposed within or behind a first window 360 (FIGS. 2, 5A, and 5B). The controller circuitry 1802 controls the wireless transmitter 1808 to transmit the operation modification signal calculated based on the characteristics or attributes of the fluid flow and the one or more conditions specified by the one or more rules to an external computing device, e.g., a Display and Data Processing Module 1810 including display and data processing software. For example, in some embodiments, if a fluid type is determined to be a different type than a desired fluid type, or if a flow rate is determined to be a different flow rate than a desired flow rate, the controller circuitry 1802 can control the wireless transmitter 1808 to transmit an operation modification signal to the Display and Data Processing Module 1810 that causes the module 1810 to display an alarm or alert or causes the module 1810 to transmit a signal back to the system 200 that stops the fluid flow. The controller circuitry 1802 can further control the wireless transmitter 1808 to transmit injection data representing a type of medication, a dose of a medication, and/or a time of a dose of a medication to the Display and Data Processing Module 1810. In some embodiments, the controller circuitry 1802 can automatically transmit the data to the module 1810 in response to an automated injection.

The Display and Data Processing Module 1810 can includes a wireless transmitter, such as a dongle-type transmitter, configured to communicate with the wireless transmitter 1808 of the base 220, and a computing device including a microcontroller and memory, such as a tablet micro-computer. The Display and Data Processing Module 1810 is configured to execute display and data processing software that comprises a message decoder and display driver, an information display, recording system and history log/memory, and a software user interface. The Display and Data Processing Module 1810 is configured to receive flow modification signals and data representing the operation of the flow sensor from the flow sensor system 200 (and clinical data from a server computer 1812 discussed below) and analyze and present the data to a user via the user interface, as well as control operations of the system 200, such as starting up or shutting down fluid flows. For example, the Display and Data Processing Module 1810 can display a type of fluid, a flow rate, a dose history, a dose time, patient information, and other characteristics or attributes associated with or related to the fluid flow based on the characteristics and attributes of the fluid flow received from the controller circuitry 1802, as well as issue alarms or alerts to a user based thereon. The Display and Data Processing Module 1810 can further transmit data representing a dose history, manually entered events, system start/stop, and/or shutdown, and/or pre-operative information to the controller circuitry 1802.

The Display and Data Processing Module 1810 is configured to communicate with a server computer 1812. The Display and Data Processing Module 1810 is configured to exchange clinical data with the server computer 1812. The server computer 1812 can include or be connected to a database storing clinical data, e.g., medical event data, patient info, alerts, etc., and/or a database storing confirmation files and formulary files, e.g., data representing device use and drug use. The server computer 1812 can be connected to or part of a hospital network services system.

In some embodiments, as described herein, the base 220 includes an activation/engagement button 350 which allows for an indication that the flow sensor 210 has been engaged with the base 220. In one embodiment, the activation/engagement button 350 signals to the control circuitry 1802 within the base 220 that the flow sensor 210 has been properly engaged with the base 220. In another embodiment, the activation/engagement button 350 signals to the control circuitry 1802 within the base 220 that the syringe 800 has been properly engaged with the flow sensor 210. The control circuitry 1802 can be configured to initiate operations or activate the flow sensor 210 in response to receiving the activation signal.

In some embodiments, as described herein, the base 220 of the flow sensor system 200 includes optics and a digital camera disposed within or behind a first window 360 (FIG. 2) capable of reading the machine readable indicia 854 provided on a syringe label 850 of an encoded syringe. An axis of the optics and digital camera extends through the first window 360. When the flow sensor 210 is properly mounted on the base 220, the machine readable indicia 854 provided on a label 850 is aligned with the axis of the optics and digital camera. For example, as shown in FIG. 18A-D, when properly mounted, the camera of the base 220 can read the machine readable indicia 854 provided on the syringe label 850. The microprocessor of the base 220 is configured to generate an operation modification signal in response to one or more attributes of the machine readable indicia 854 matching one or more conditions specified by one or more rules. For example, if a type and/or dose of the medicament to be dispensed and indicated by the indicia 854 satisfies the one or more conditions specified by one or more rules, e.g., a proper dose at a proper time for a particular patient. The wireless transmitter of the base 220 is configured to transmit the operation modification signal to an external device, such as the display and data processing module 1810. The Display and Data Processing Module 1810 is configured to modify one or more operating parameters based on the operation modification signal. For example, the Display and Data Processing Module 1810 can issue an alarm or alert if the type, dose, or time of the medicament does not satisfy the one or more conditions specified by the one or more rules. The Display and Data Processing Module 1810 can issue a safety alarm or alert command and turn on indicators in the base 220 to alert a clinician visually, at the point of syringe attachment to the flow sensor, providing immediate indication of a cautionary condition and allowing the clinician an opportunity to modify his/her treatment, such as a drug injection, to avoid an incorrect dosage or delivery.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A system for sensing medicament delivery and transmitting an operation modification signal having at least two separable components comprising:
   a first component comprising a flow sensor having:
      a fluid port having a flow tube;
      a fluid inlet at a first end of the flow tube adapted to couple to an outlet of a fluid source;
      a fluid outlet at a second end of the flow tube adapted to deliver fluid from the fluid source to a fluid pathway that provides fluid to a patient;
      at least one sensor to characterize at least one attribute of the fluid from the fluid source; and
      at least one pin in electrical communication with the at least one sensor; and
   a second component comprising a base having:
      at least one contact;
      a controller in electrical communication with the at least one contact that generates at least one operation modification signal in response to at least one attribute matching at least one condition specified by at least one rule;
      a transmitter for wirelessly transmitting the operation modification signal to at least one device, the operation modification signal, when received by the at least one device, causing the at least one device to modify at least one operating parameter; and
      a cross-component electrical circuit,
      wherein the flow sensor is mountable onto the base and said cross-component electrical circuit is a connection made by said contacts engaging said pins.

2. The system according to claim 1, wherein the flow sensor further comprises end fittings adapted for securing the flow tube to the end fittings and a first piezo element and a second piezo element that are mounted to the end fittings.

3. The system according to claim 1, wherein said flow tube is a stainless steel material.

4. The system according to claim 2, wherein said first piezo element and said second piezo element are annular in shape and encircle the flow tube at each respective mounting point.

5. The system according to claim 1, wherein said flow sensor is disposed of after use to generate one operation modification signal.

6. The system according to claim 5, wherein the base is used with a different flow sensor.

7. The system according to claim 1, wherein the flow sensor further comprises cantilevered wings adapted for securing the flow sensor to the base.

8. The system according to claim 1, wherein the flow sensor further comprises a follower and said base further comprises a cam wherein said follower follows at least a portion of said cam when said flow sensor is mounted to the base.

9. The system according to claim 1, wherein the flow sensor further comprises an opening and said base further comprises a protrusion wherein said opening is sized and shaped to engage said protrusion and said protrusion enters said opening when said flow sensor is mounted to said base.

10. The system according to claim 8, wherein the flow sensor further comprises an opening and said base further comprises a protrusion wherein said opening is sized and shaped to engage said protrusion and said cam is adapted to move said at least one pin away from said protrusion while said protrusion enters said opening when said flow sensor is mounted to said base.

11. The system according to claim 10, wherein the flow sensor further comprises at least one cantilevered wing having a tab adapted for securing the flow sensor to the base by engagement of said tab to at least one lip in the base.

12. The system according to claim 9, wherein the flow sensor further comprises at least one cantilevered wing having a tab adapted for securing the flow sensor to the base by engagement of said tab to at least one lip in the base.

13. The system according to claim 12, wherein the at least one cantilevered wing is deflectable in a direction to allow said tab to release from said at least one lip, thereby allowing said flow sensor to become de-mounted from said base.

14. The system according to claim 11, wherein the at least one cantilevered wing is deflectable in a direction to allow said tab to release from said at least one lip thereby allowing said flow sensor to become de-mounted from said base.

15. The system according to claim 12, wherein the at least one cantilevered wing is a pair of cantilevered wings.

16. The system according to claim 11, wherein the at least one cantilevered wing is a pair of cantilevered wings.

17. The system according to claim 12, wherein the at least one cantilevered wing is a pair of cantilevered wings and each respective wing is arranged opposite each other and said opening is spaced away from said wings and said opening has a center position which bisects a distance between said cantilevered wings and the follower is a pair of followers and each respective follower is arranged opposite each other on said flow sensor.

18. The system according to claim 11, wherein the at least one cantilevered wing is a pair of cantilevered wings and each respective wing is arranged opposite each other and said opening is spaced away from said wings and said opening has a center position which bisects a distance between said cantilevered wings.

19. The system according to claim 1, further comprising a seal for a liquid-tight engagement between said flow sensor and said base, wherein said seal surrounds said cross-component electrical circuit, thereby sealing said cross-component electrical circuit from contamination by a liquid.

20. The system according to claim 1, wherein the flow sensor further comprises cantilevered wings having a tab adapted for securing the flow sensor to the base by engagement of said tab to a lip in the base.

21. A system for sensing medicament delivery and transmitting an operation modification signal having at least two separable components comprising:
 a first component comprising a flow sensor having:
  a fluid port having a flow tube;
  a fluid inlet at a first end of the flow tube adapted to couple to an outlet of a fluid source;
  a fluid outlet at a second end of the flow tube adapted to deliver fluid from the fluid source to a fluid pathway that provides fluid to a patient;
  at least one sensor to characterize at least one attribute of the fluid from the fluid source; and
  a movable detector which detects a coupling of the outlet of said fluid source to said fluid inlet of said flow sensor; and
 a second component comprising a base having:
  a controller that generates the operation modification signal in response to at least one attribute matching at least one condition specified by at least one rule;
  a switch for activating said controller; and
  a transmitter for wirelessly transmitting the operation modification signal to at least one device, the operation modification signal, when received by the at least one device, causing the at least one device to modify at least one operating parameter,
 wherein the flow sensor is mountable onto the base and said movable detector engages said switch, thereby activating said controller.

22. The system according to claim 21, wherein the flow sensor further comprises cantilevered wings adapted for securing the flow sensor to the base.

23. The system according to claim 21, wherein the flow sensor further comprises a follower and said base further comprises a cam wherein said follower follows at least a portion of said cam when said flow sensor is mounted to the base.

24. The system according to claim 21, wherein the flow sensor further comprises an opening and said base further comprises a protrusion wherein said opening is sized and shaped to engage said protrusion and said protrusion enters said opening when said flow sensor is mounted to said base.

25. The system according to claim 23, wherein the flow sensor further comprises an opening and said base further comprises a protrusion wherein said opening is sized and shaped to engage said protrusion and said cam is adapted to move a pin away from said protrusion while said protrusion enters said opening when said flow sensor is mounted to said base.

26. The system according to claim 21, wherein the flow sensor further comprises cantilevered wings having a tab adapted for securing the flow sensor to the base by engagement of said tab to a lip in the base.

27. The system according to claim 21, wherein the movable detector further comprises a cantilevered beam protruding from a portion of said flow sensor, said cantilevered beam having a free end which engages said switch by deflection of said cantilevered beam.

28. The system according to claim 21, wherein the movable detector further comprises a cantilevered beam protruding from a portion of said flow sensor, said cantilevered beam having a free end having an outlet engaging portion extending in a direction generally perpendicular to said cantilevered beam.

29. The system according to claim 28, wherein the movable detector further comprises a switch engaging portion of said free end extending in a direction generally opposite to said outlet engaging portion.

30. A system for sensing medicament delivery and transmitting an operation modification signal having at least two separable components comprising:
 a first component comprising a flow sensor having:
  a fluid port having a flow tube;
  a fluid inlet at a first end of the flow tube adapted to couple to an outlet of a fluid source having a target;
  a fluid outlet at a second end of the flow tube adapted to deliver fluid from the fluid source to a fluid pathway that provides fluid to a patient; and
  at least one sensor to characterize at least one attribute of the fluid from the fluid source; and a second component comprising a base having:
   a portal;
   a controller in communication with an optical sensor having an axis that extends through said portal and inputs a signal to said controller and wherein said controller generates at least one operation modification signal in response to the at least one attribute matching at least one condition specified by at least one rule; and
   a transmitter for wirelessly transmitting the operation modification signal to at least one device, the operation modification signal, when received by the at least one device, causing the at least one device to modify at least one operating parameter,
wherein when the flow sensor is mounted onto the base said optical sensor axis is aligned with said target.

31. The system according to claim 30, wherein the target is indicia on said outlet of said fluid source.

32. The system according to claim 30, wherein the flow sensor further comprises a follower and said base further comprises a cam wherein said follower follows at least a portion of said cam when said flow sensor is mounted to the base.

33. The system according to claim 30, wherein the flow sensor further comprises an opening and said base further comprises a wedge-like protrusion wherein said opening is sized and shaped to accommodate a widest portion of said wedge-like protrusion and said optical sensor axis is aligned with said target when said widest portion enters said opening as said flow sensor is mounted to said base.

34. The system according to claim 32, wherein the flow sensor further comprises an opening and said base further comprises a protrusion wherein said opening is sized and shaped to engage said protrusion and said cam is adapted to move a pin away from said protrusion while said protrusion enters said opening when said flow sensor is mounted to said base, and when said follower is at a final position of said cam, said optical sensor axis is aligned with said target.

* * * * *